US012263489B2

(12) United States Patent
Shikata et al.

(10) Patent No.: US 12,263,489 B2
(45) Date of Patent: Apr. 1, 2025

(54) MANUFACTURING METHOD OF THE OPERATION PIPE

(71) Applicant: SHIMADZU CORPORATION, Kyoto (JP)

(72) Inventors: Masamitsu Shikata, Kyoto (JP); Ayaka Minamimoto, Kyoto (JP); Akira Muramatsu, Kyoto (JP); Masaki Kanai, Kyoto (JP); Seiya Fujiwara, Kyoto (JP); Tetsuo Ohashi, Kyoto (JP); Hiroyuki Jikuya, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 411 days.

(21) Appl. No.: 17/840,568

(22) Filed: Jun. 14, 2022

(65) Prior Publication Data

US 2022/0355310 A1    Nov. 10, 2022

Related U.S. Application Data

(63) Continuation of application No. 16/782,064, filed on Feb. 5, 2020, now abandoned.

(30) Foreign Application Priority Data

Mar. 9, 2019   (JP) ................................ 2019-043228

(51) Int. Cl.
*B03C 1/12*      (2006.01)
*B01D 15/38*   (2006.01)
(Continued)

(52) U.S. Cl.
CPC ............ *B03C 1/12* (2013.01); *B01D 15/3819* (2013.01); *B01D 15/3885* (2013.01);
(Continued)

(58) Field of Classification Search
CPC ........... B03C 1/12; B03C 1/01; B03C 1/0332; B03C 1/0335; B03C 1/288; B03C 1/30;
(Continued)

(56) References Cited

U.S. PATENT DOCUMENTS 9,517,472 B2   12/2016   Ohashi
10,073,108 B2   9/2018   Ohashi
(Continued)

FOREIGN PATENT DOCUMENTS

CN    103269787 A  *  8/2013  ............ B01L 3/5025
CN    105772122         7/2016
(Continued)

OTHER PUBLICATIONS

Machine-generated English translation of CN 103269787, generated on Sep. 27, 2024.*

(Continued)

*Primary Examiner* — Fred Prince
(74) *Attorney, Agent, or Firm* — JCIPRNET

(57) ABSTRACT

A manufacturing method of an operation pipe, which use a gel to perform operations such as separation, extraction, purification, elution, recovery, analysis and the like of target components that are biological components such as nucleic acids. More specifically, a manufacturing method of an operation pipe, with which it is possible to perform operations such as separation, extraction, purification, elution, recovery, analysis and the like of target components in a sealable pipe by operating magnetic particles in the pipe under a magnetic field from outside of the pipe.

9 Claims, 8 Drawing Sheets

Specification includes a Sequence Listing.

(51) Int. Cl.
*B01L 3/00* (2006.01)
*B01L 9/06* (2006.01)
*B03C 1/01* (2006.01)
*B03C 1/03* (2006.01)
*B03C 1/033* (2006.01)
*B03C 1/28* (2006.01)
*B03C 1/30* (2006.01)
*C12N 15/10* (2006.01)
*C12Q 1/68* (2018.01)
*C12Q 1/6806* (2018.01)
*C12Q 1/6816* (2018.01)
*C12Q 1/6865* (2018.01)

(52) U.S. Cl.
CPC ............... *B01L 3/5085* (2013.01); *B01L 9/06* (2013.01); *B03C 1/01* (2013.01); *B03C 1/0332* (2013.01); *B03C 1/0335* (2013.01); *B03C 1/288* (2013.01); *B03C 1/30* (2013.01); *C12N 15/1013* (2013.01); *C12Q 1/6806* (2013.01); *C12Q 1/6816* (2013.01); *C12Q 1/6865* (2013.01); *B01L 3/5025* (2013.01); *B01L 2200/0647* (2013.01); *B01L 2400/043* (2013.01); *B03C 2201/18* (2013.01); *B03C 2201/26* (2013.01); *C12Q 2563/107* (2013.01)

(58) Field of Classification Search
CPC ............ B03C 2201/18; B03C 2201/26; B01D 15/3819; B01D 15/3885; B01L 3/5085; B01L 9/06; B01L 3/5025; B01L 2200/0647; B01L 2400/043; C12N 15/1013; C12Q 1/6806; C12Q 1/6816; C12Q 1/6865; C12Q 2563/107; C12Q 2563/149; C12Q 2523/308

USPC ......................................... 210/222, 223, 338
See application file for complete search history.

(56) References Cited

U.S. PATENT DOCUMENTS

| | | | |
|---|---|---|---|
| 10,533,170 B2 | 1/2020 | Ohashi et al. | |
| 2016/0180998 A1* | 6/2016 | Kanai | ................ G01N 35/0098 210/222 |

FOREIGN PATENT DOCUMENTS

| | | | | |
|---|---|---|---|---|
| CN | 106102898 | | 11/2016 | |
| CN | 108405002 B | * | 9/2020 | ............ B01L 3/0275 |
| JP | 2017049149 | | 3/2017 | |
| WO | 2012086243 | | 6/2012 | |

OTHER PUBLICATIONS

Machine-generated English translation of CN 108405002, generated on Sep. 27, 2024.*

"Office Action of Counterpart China Divisional Application", issued on May 9, 2023, with English translation thereof, pp. 1-14.

"Office Action of Japan Counterpart Application" with English translation thereof, issued on Jul. 4, 2022, p. 1-p. 6.

"Office Action of Japan Counterpart Application", issued on Dec. 13, 2022, with English translation thereof, pp. 1-8.

"Office Action of Counterpart China Divisional Application No. 202210348579.5", issued on Aug. 1, 2023, with English translation thereof, pp. 1-20.

* cited by examiner

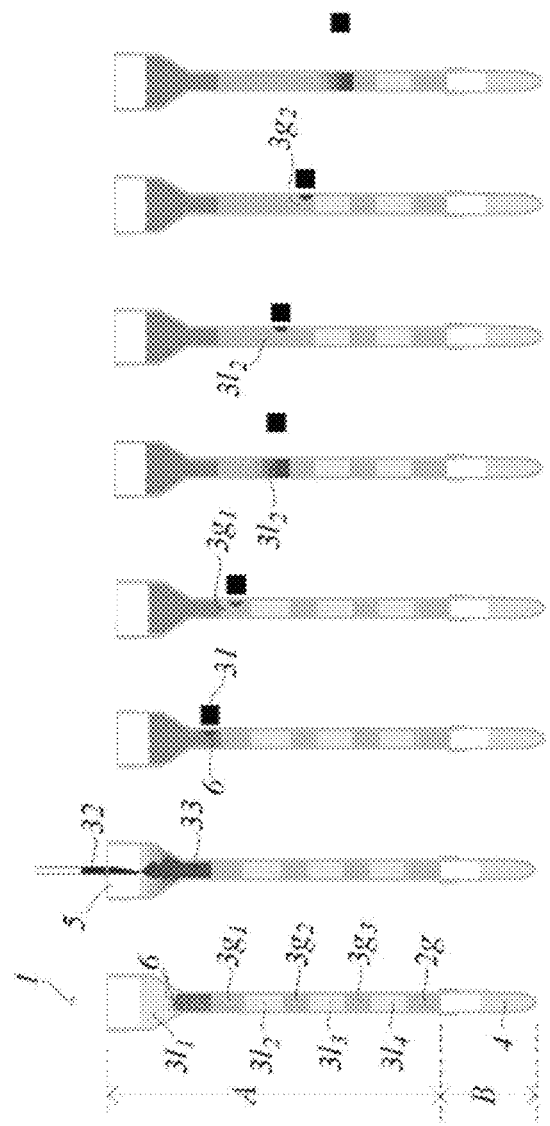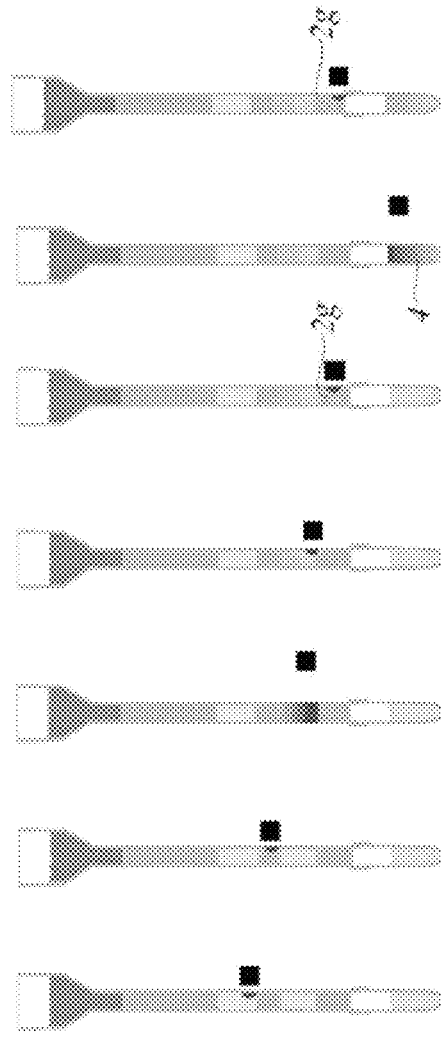

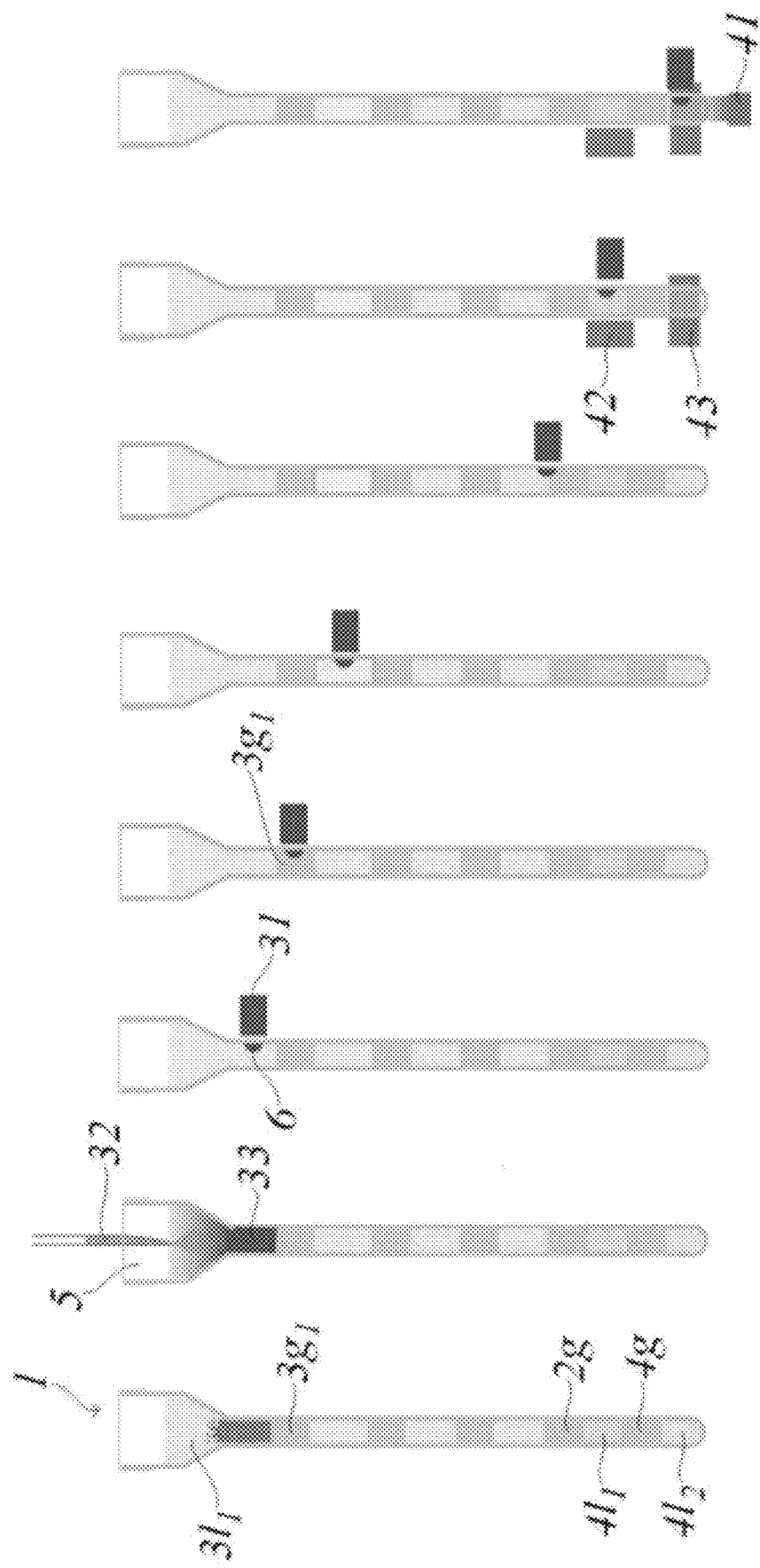

lane M: 100bp ladder molecular weight marker
lane P: liquid after PCR reaction (5 µL)

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: synthetic RT-PCR primer

<400> SEQUENCE: 1
gcgctgccaa ggctgtgggc aagg                                      24

<210> SEQ ID NO 2
<211> LENGTH: 24
<212> TYPE: DNA
<213> ORGANISM: Artificial Sequence
<220> FEATURE:
<223> OTHER INFORMATION: synthetic RT-PCR primer

<400> SEQUENCE: 2
ggccctccga cgcctgcttc acca                                      24
```

MANUFACTURING METHOD OF THE OPERATION PIPE

CROSS-REFERENCE TO RELATED APPLICATION

This application is a Continuation application of and claims the priority benefit of a prior U.S. application Ser. No. 16/782,064, filed on Feb. 5, 2020, now pending. The prior application Ser. No. 16/782,064 claims the priority benefit of Japan application serial no. 2019-043228, filed on Mar. 9, 2019. The entirety of each of the above-mentioned patent applications is hereby incorporated by reference herein and made a part of this specification.

BACKGROUND OF THE DISCLOSURE

Technical Field

The disclosure relates to a manufacturing method of an operation pipe, which use a gel to perform operations such as separation, extraction, purification, elution, recovery, analysis and the like of target components that are biological components such as nucleic acids. More specifically, the disclosure relates to a manufacturing method of an operation pipe, with which it is possible to perform operations such as separation, extraction, purification, elution, recovery, analysis and the like of target components in a sealable pipe by operating magnetic particles in the pipe under a magnetic field from outside of the pipe.

Related Art

By giving various chemical affinity to surfaces of water-insoluble fine particles having a diameter of 0.5 μm to ten-odd micrometres, the target components can be separated, extracted, purified, eluted, recovered and the like. In addition, target cells can also be recovered by recognizing specific cell surface molecules. Based on these findings, fine particles in which functional molecules having affinity for the target components are introduced onto the particle surface are commercially available. Among these fine particles, ferromagnets of which the particle material is iron oxide or the like can recover the target components by a magnet, and have a feature advantageous for automation of the extraction and purification of the target components because centrifugation is not required.

For example, a system for continuously performing nucleic acid extraction from cells to analysis performed by gene amplification reaction in one device is commercially available. For example, in GeneXpert System (non-patent literature 1) of Cepheid, USA, the nucleic acid extraction to the analysis performed by gene amplification reaction are performed in one cartridge-type device, and the maximum number of specimens simultaneously processed is 16. In addition, for example, in Simplexa (non-patent literature 2) of 3M Corporation, the nucleic acid extraction to PCR can be performed in one disk-shaped device, and 12 specimens can be fixed on one disk. However, these devices have a small number of specimens simultaneously processed, and the devices themselves are complicated and expensive to manufacture, making the devices impractical. In addition, the device size is large and thus the entire system is also large, making the devices impractical in terms of mobility from an installation location.

Magnetic particles are commercially available as a part of reagents that are extraction and purification kits. The kit is configured by a plurality of reagents contained in separate containers, and the user collects and dispenses the reagents by a pipette or the like during use. Even in a case of an automated device, in a currently marketed device, liquid collection is mechanically performed by pipetting operations. For example, a system (non-patent literature 3) for performing nucleic acid extraction using magnetic particles is commercially available from Precision System Science Co., Ltd. These pipetting operations are accompanied by generation of aerosols. The generation of aerosol increases the risk of contamination that hinders analysis. The same also applies to a case in which the liquid collection is mechanically performed by pipetting operations in an automated device. In this case, since pollution source is accumulated in the device due to the generation of aerosols, it is necessary to periodically clean the device. However, in the device automated by a pipette-type dispensing mechanism, the structure is complicated, and it is difficult to completely remove the pollution source.

In general, the commercially available magnetic particles enable separation and recovery of target components or specific cells from a sample, but it is necessary to perform analysis of the recovered material in another system such as a real-time PCR device, a mass spectrometer, a flow cytometry or the like. In the system which is commercially available from Precision System Science Co., Ltd for using magnetic particles to perform nucleic acid extraction, even the recovery of purified nucleic acids can be performed, but it is necessary to perform the analysis performed by gene amplification reaction and the like in another system such as a real-time PCR device or the like. Furthermore, in this system, the dispensing using a pipette-type dispenser is performed in an open system, and thus is always accompanied by a risk of contamination.

In order to solve the above problems, an operation pipe that is small and has low running cost and a device equipped with the operation pipe are reported, with which it is possible to perform extraction and purification of target components in a completely sealed container while avoiding contamination or possible to analyze the target components in the same container while keeping the sealed state following the extraction and purification (patent literature 1). A sealable narrow pipe constituting the operation pipe is filled with one or more liquid reagents partitioned by a water-insoluble gel substance without using a dispenser accompanied by the generation of aerosols, and the magnetic particles present in the liquid reagents filled in the narrow pipe are moved by a magnetic field applying part operable from outside of the narrow pipe and pass through a water-insoluble gel substance layer.

LITERATURE OF RELATED ART

Patent Literature

[Patent literature 1] WO 2012/086243

Non-Patent Literature

[Non-patent literature 1] Clinical Chemistry 51: 882-890, 2005, Mar. 3, 2005

[Non-patent literature 2] "FDA Issues Another Emergency Use Authorization for Commercial H1N1 Flu Test to Quest Diagnostics' Focus Diagnostics", Focus Diagnostics Co., Ltd, Oct. 17, 2009

[Non-patent literature 3] "GC series Magtration Genomic DNA Whole Blood", Precision System Science Co., Ltd, December, 2008

SUMMARY

In the operation pipe disclosed in patent literature 1, a sample containing magnetic particles is introduced from an open end of a pipe constituting the operation pipe. The sample is obtained by crushing or dissolving biological samples such as blood or cells, and biological components such as nucleic acids is adsorbed to the magnetic particles. The magnetic particles adsorbing the biological components can be collected by an external magnetic field. Furthermore, the magnetic particles adsorbing the biological components can be moved in the pipe by movement of the external magnetic field. Inside the pipe, a cleaning liquid layer for washing away contaminants contained in the biological sample and an elution liquid layer for liberating the biological components such as nucleic acids are filled as liquid reagent layers, and the cleaning liquid layer and the elution liquid layer are partitioned by a water-insoluble gel layer so as not to be mixed. When the external magnetic field is gently moved, the magnetic particles adsorbing the biological components such as nucleic acids can follow the movement and pass through the gel layer without mixing the cleaning liquid and the elution liquid. On the other hand, when the external magnetic field is rapidly reciprocated, the magnetic particles in the liquid reagent layer cannot follow the movement of the external magnetic field and are dispersed in the liquid. By this operation, the contaminant components contained in the biological sample are washed away in the cleaning liquid layer, and the biological components such as nucleic acids are liberated from the magnetic particles in the elution liquid layer.

The cleaning liquid layer, the eluent liquid layer, and the water-insoluble gel layer filled in the pipe constituting the operation pipe disclosed in patent literature 1 are filled based on a distance in the longitudinal direction of the pipe. The reason is that accurate setting of a movement position can be made based on the distance in the setting of a driving program for moving the external magnetic field. On the other hand, when an inner diameter of the pipe varies, a volume of the liquid reagent in the liquid reagent layer varies due to the variation. In particular, when the liquid reagent is an elution liquid that liberates biological components such as nucleic acids, variation in the volume of the elution liquid causes variation in the concentration of the biological components such as nucleic acids eluted in the elution liquid. As a result, accurate recovery rate evaluation of the biological components such as nucleic acids is hindered.

The disclosure provides an operation pipe and a device equipped with the operation pipe, which enable accurate recovery rate evaluation of biological components such as nucleic acids recovered in an elution liquid.

That is, the disclosure includes the following aspects.

[1]
A manufacturing method of an operation pipe for operating target components, including: providing a hollow pipe having a closable open end for supplying a sample containing the target components on one side and a closed end on the other side, and having an operation pipe portion a on the open end side and a recovery pipe portion b on the closed end side; filling a recovery medium in the recovery pipe portion b so that a first gel layer and a first aqueous liquid layer which is in contact with the closed end are multi-layered, wherein the first aqueous liquid layer in contact with the closed end has a predetermined volume, and the layer length of the first gel layer is determined by the length in the longitudinal direction of the hollow pipe; and filling an operation medium in the operation pipe portion a so that second gel layers and second aqueous liquid layers are alternately multi-layered in the longitudinal direction of the hollow pipe, wherein a layer length of each of the second gel layers and a layer length of each of the second aqueous liquid layers are determined by the length in the longitudinal direction of the hollow pipe.

The open end is preferably closed so that all or a part of the open end can be opened and closed. In FIGS. 1B and 1C, an example of a preferable open end, an example of the hollow pipe having the operation pipe portion a on the open end side and the recovery pipe portion b on the closed end side, and an example of the operation pipe are shown.

[2]
The manufacturing method of the operation pipe according to [1], wherein an inner diameter of the hollow pipe is 0.1 mm-5 mm.

[3]
The manufacturing method of the operation pipe according to [1] or [2], wherein a volume of the first aqueous liquid layer in contact with the closed end is 1 µL-1000 µL.

[4]
The manufacturing method of the operation pipe according to any one of [1] to [3], wherein the operation pipe portion a and the recovery pipe portion b are separable.

[5]
The manufacturing method of the operation pipe according to any one of [1] to [4], wherein the material of the hollow pipe is selected from a group consisting of polyethylene, polypropylene, fluororesin, polyvinyl chloride, polystyrene, polycarbonate, acrylonitrile-butadiene-styrene copolymer, acrylonitrile-styrene copolymer, acrylic resin, polyvinyl acetate, polyethylene terephthalate, cyclic polyolefin, and glass.

[6]
The manufacturing method of the operation pipe according to any one of [1] to [5], wherein an inner diameter of the open end is larger than an inner diameter of the operation pipe portion a and an inner diameter of the recovery pipe portion b.

[7]
The manufacturing method of the operation pipe according to any one of [1] to [6], wherein the hollow pipe has optical transparency.

[8]
The manufacturing method of the operation pipe according to any one of [1] to [7], wherein surface roughness of an inner surface of the hollow pipe is 0.1 µm or less.

[9]
The manufacturing method of the operation pipe according to any one of [1] to [8], wherein the layer length of the first gel layer and the layer length of each of the second gel layers are 1-20 mm.

[10]
The manufacturing method of the operation pipe according to any one of [1] to [9], wherein the layer length of each of the second aqueous liquid layers is 0.5-30 mm.

Effect

According to the disclosure, the volume of the elution liquid that liberates biological components such as nucleic acids is constant, the elution liquid being filled in the recovery pipe portion b in a hollow pipe constituting an operation pipe and constituting an aqueous liquid layer in contact with a closed end of the hollow pipe, and thus accurate recovery rate evaluation of the biological components such as nucleic acids recovered in the elution liquid can be made. A gel layer and an aqueous liquid layer other than the aqueous liquid layer in contact with the closed end of the hollow pipe, which is the elution liquid for liberating the biological components such as nucleic acids, are filled with a thickness determined by the length in the longitudinal direction of the hollow pipe, and thus it is unnecessary to change or modify a drive program for moving an external magnetic field.

BRIEF DESCRIPTION OF THE DRAWINGS

FIGS. 3A to 3O show a process in which the operation pipe of the disclosure shown in FIGS. 1A to 1C is used to extract and purify nucleic acids from a nucleic acid-containing sample.

FIGS. 4A to 4H show a process in which another example of the operation pipe of the disclosure is used to extract and purify nucleic acids from the nucleic acid-containing sample, and analysis performed by a reverse transcription reaction and a PCR reaction are further performed.

DESCRIPTION OF THE EMBODIMENTS

[1. Operation of Target Components]
[1-1. Target Components]

Target components operated in the disclosure is not particularly limited as long as the target components can be operated in common aqueous liquids, emulsions, or hydrogels, and may be any in vivo components and non-in vivo components. The in vivo components include biomolecules such as nucleic acids (including DNA and RNA), proteins, lipids, and sugars. The non-in vivo components include non-biomolecules such as artificial (both chemical and biochemical) modifiers, labelled bodies, mutants and the like of the biomolecules, non-biomolecules derived from natural products, and other components that can be operated in an aqueous system.

The target components can usually be provided in the form of a sample containing the target components. The sample include, for example, biological samples such as animal and plant tissues, body fluids and excreta, and biomolecule-containing bodies such as cells, protozoa, fungi, bacteria and viruses. The body fluids include blood, sputum, cerebrospinal fluid, saliva, and milk and may be combinations thereof; and the excreta include feces, urine, and sweat and may be combinations thereof. The cells include leukocytes and platelets in blood or exfoliated cells of oral cells and other mucosal cells and may be combinations thereof. These samples can also be obtained as clinical swabs. In addition, the above sample can also be prepared, for example, in the form of a liquid mixture of a cell suspension, a homogenate, and a cell lysate. In addition, the sample containing the target components can also be obtained by applying treatments such as modification, labelling, fragmentation, and mutation to the above sample.

The sample containing the target components may also be prepared in advance by subjecting the above sample to pre-treatment. The pre-treatment includes, for example, a treatment for performing extraction, separation, and purification of the target components or the target component-containing body from the sample containing the target components, and the like. However, since this pre-treatment can be performed in the operation pipe of the disclosure, it is not always necessary to perform the pre-treatment before the sample is added into the operation pipe. By performing the pre-treatment in the operation pipe of the disclosure, a contamination problem that is a concern in the pre-treatment of the sample can be avoided.

[1-2. Operation]
[1-2-1. Operation Form]

Figure 1A:
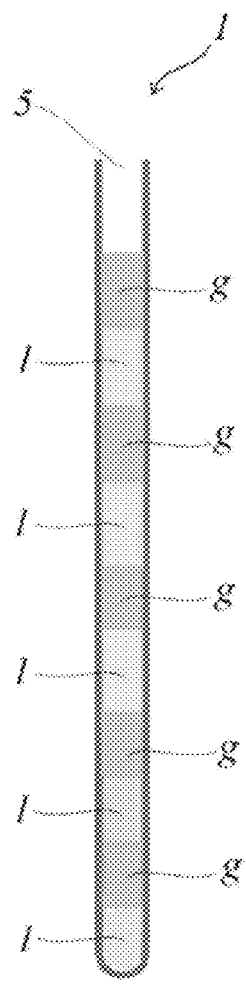
FIGS. 1A, 1B, and 1C are longitudinal-sectional views of examples of an operation pipe of the disclosure. A and B described in FIG. 1C respectively represent an operation portion A and a recovery portion B. The operation portion A includes an operation pipe portion a corresponding in a hollow pipe and an operation medium filled in the pipe portion a. The recovery portion B includes a recovery pipe portion b corresponding in the hollow pipe and a recovery medium filled in the pipe portion b.
Figure 1B:
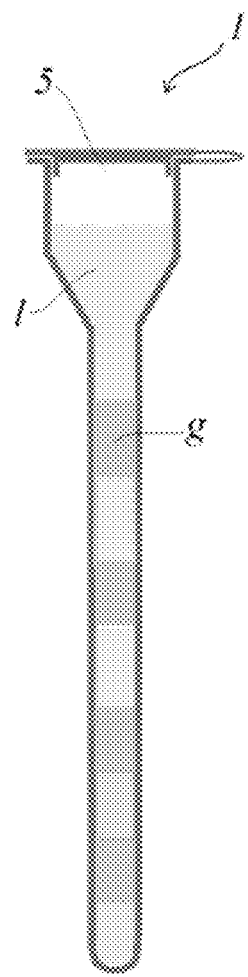
Figure 1C:
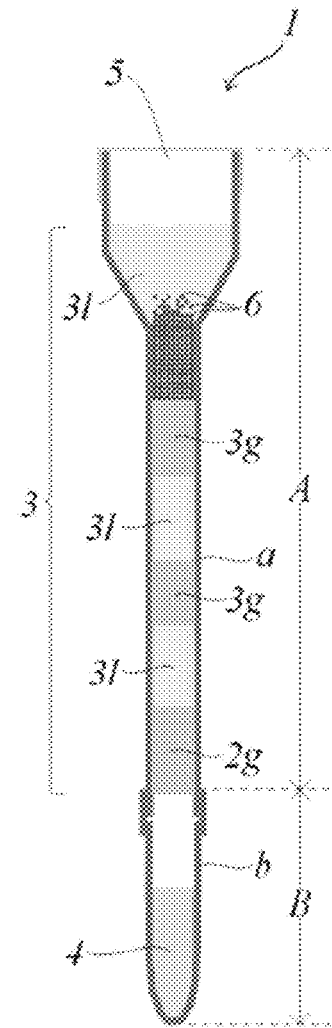

In the disclosure, the sample containing the target components is added to the operation pipe illustrated as 1 in FIGS. 1A to 1C, and the target components are operated in the operation pipe. Operations of the target components in the disclosure include supplying the target components to various treatments and transporting the target components among a plurality of environments for performing the various treatments. The operation pipe is filled with gel layers and aqueous liquid layers. For example, in the form illustrated in FIGS. 1A to 1C, the layers represented by 2g and 3g consist of gels (gel plugs), and the layer represented by 3l consists of an aqueous liquid. The layer represented by 4 is an aqueous liquid layer in contact with the closed end of a hollow pipe constituting the operation pipe of the disclosure, and may also be a hydrogel as long as the aqueous liquid can maintain a gel state. The aqueous liquid and the hydrogel construct an environment for performing a treatment of the target components. Accordingly, more specifically, the operations of the target components in the disclosure include supplying the target components to treatments in the aqueous liquid or hydrogel and transporting the target components among a plurality of environments for performing the treatments via a gel plug.

[1-2-2. Treatment of Target Components]

The treatments to which the target components are supplied include the treatment accompanied by a substance change of the target components and the treatment accompanied by a physical change of the target components.

The treatment accompanied by a substance change of the target components may be any treatment as long as a different substance is newly generated by generating or breaking a bond between substrates. More specifically, a chemical reaction and a biochemical reaction are included. The chemical reaction may be any reaction accompanied by compounding, decomposition, oxidation and reduction. In the disclosure, generally, treatments that are performed in an aqueous liquid are included. The biochemical reaction may be any reaction accompanied by a change of biological substances, and usually refers to an in vitro reaction. For example, reactions based on a synthesis system, a metabolic system and an immune system of biological substances such as nucleic acids, proteins, lipids, sugars and the like are included.

The treatment accompanied by a physical change of the target components may be any treatment not accompanied by the above substance change. More specifically, denaturation (for example, when the target components are biopolymers or other polymers containing nucleic acids or proteins), dissolution, mixing, emulsification, dilution, and the like of the target components are included.

Accordingly, operations such as separation, extraction, purification, elution, recovery, and analysis of the target components can be performed by the treatment in the disclosure. By these operations, isolation, detection, identification and the like of the target components can be finally performed.

The treatments in the disclosure include not only the desired treatments (treatments in a process in which effects of isolation, detection, identification and the like of the target components are directly obtained), but also a pre-treatment and/or a post-treatment associated therewith as necessary. For example, when the target components are nucleic acids, a nucleic acid amplification reaction or a nucleic acid amplification reaction and analysis of amplification products are performed, but extraction (cell lysis) and/or purification (cleaning) of the nucleic acids from a nucleic acid-containing sample and the like are essential as the pre-treatments thereof. In addition, recovery and the like of the amplification products may be performed as the post-treatments.

[1-2-3. Transport of Target Components] The transport of the target components is performed by magnetic particles and a magnetic field applying part. The magnetic particles are present in the operation pipe during operation, and can transport the target components by moving the target components in the operation pipe in a state that the target components are captured by being bound and absorbed to the surface of the magnetic particles. The magnetic particles can be dispersed in the aqueous liquid layer in the operation pipe, and are usually aggregated in the aqueous liquid layer due to generation of a magnetic field from outside of the operation pipe by the magnetic field applying part. The aggregated magnetic particles can move along with changes of the magnetic field that is generated from outside of the operation pipe by the magnetic field applying part. The aggregated magnetic particles can move in the gel layer. By utilizing the thixotropic property (thixotropic property) of the gel described in 3-2-3, the aggregated magnetic particles can pass through the gel layer without destroying the gel layer. In the gel, the aggregated magnetic particles are accompanied by the target components by binding or adsorption. Strictly speaking, the group of the aggregated magnetic particles is coated with a very small amount of aqueous liquid. Accordingly, components other than the target components may be accompanied.

However, since the amount of the coated aqueous liquid is very small, almost no aqueous liquid is contained. Therefore, the transport of the target components can be performed very efficiently.

[2. Operation Pipe]

[2-1. Structure of Operation Pipe]

The structure of the operation pipe of the disclosure is described with reference to FIGS. 1A-1C (in the following description, the vertical direction uses FIGS. 1A-1C as a reference). The hollow pipe constituting the operation pipe has an upper end opened for sample feeding, and the open end is preferably closable from the viewpoint of contamination. A lower end of the hollow pipe is a closed end. Usually, the hollow pipe constituting the operation pipe has a substantially circular cross section, but pipes having other shapes of cross section are not excluded. The pipe is filled with an operation medium in which aqueous liquid layers 1 and gel layers g are alternately multi-layered in the longitudinal direction of the pipe. FIGS. 1A-1C illustrate three aspects FIGS. 1A-1C in which forms of an upper portion and a lower portion of the operation pipe are different. However, the upper portion and the lower portion can be arbitrarily combined and are not limited to the combinations shown in FIGS. 1A-1C.

The upper open end of the pipe is a sample supply portion 5 for supplying the sample containing the target components, and the sample supply portion 5 that is an open end may be temporarily opened (see FIG. 1A), or all or a part of the sample supply portion 5 may be openably closed (shown in FIG. 1B). By using a septum having a check valve function as an example that a part is openably closed, it is possible to supply a sample by puncturing with an injection needle that can substantially maintain a sealed state (shown in FIG. 1C). It is preferable to close the sample supply portion 5 that is an open end because a completely sealed system can be constructed. By constructing a completely closed system, contamination from outside during operation can be prevented, and thus the operation pipe is very effective. The inner diameter of the sample supply portion 5 may be the same as an inner diameter of the pipe portion a filled with the gel layer and the aqueous liquid layer which are operation mediums (shown in FIG. 1A), or may be formed to have a wider inner diameter from the viewpoint of operability during supply of the sample (shown in FIGS. 1B and 1C).

In the aspects illustrated in FIGS. 1A and 1B, the pipe is integrally formed. In the aspect illustrated in FIG. 1C, the pipe is configured by the operation pipe portion a and the recovery pipe portion b. The upper end and the lower end of the operation pipe portion a are open. The upper end of the recovery pipe portion b is open and the lower end is closed. In the operation pipe portion a and the recovery pipe portion b, one end of the pipe portion a and the open end of the pipe portion b are connected. The operation pipe portion a and the recovery pipe portion b may have a separable shape, or may have a shape not considering separation (a shape that cannot be separated).

The operation pipe portion a is filled with a gel layer 2g that closes one end and a multi-layer that is multi-layered on the gel layer 2g, that is, an operation medium 3. The operation medium 3 is configured so that aqueous liquid layers 3l and gel layers 3g are alternately multi-layered. The part configured by the operation pipe portion a and the operation medium that is the filling of the operation pipe portion a is described as an operation portion A. The recovery pipe portion b is filled so that a gel layer in contact with the operation pipe portion a and an aqueous liquid layer in contact with the closed end at the lower end are multi-layered. The aqueous liquid layer in contact with the closed end is represented by a recovery medium 4. The part configured by the recovery pipe portion b, the recovery medium 4 that is the filling of the recovery pipe portion b, and the gel layer in contact with the operation pipe portion a is described as a recovery portion B. The operation portion A and the recovery portion B may be provided in a connected state or may be provided in an independent state. In the recovery portion B, the gel layer in contact with the operation pipe portion a has a function of preventing the recovery medium 4 from flowing out in a state that the recovery portion B is separated or independent. The recovery portion B may be configured by a recovery pipe portion b that is not filled with the gel layer and is filled only with the aqueous liquid layer.

[2-2. Size of Operation Pipe]

The approximate inner diameter of the hollow pipe constituting the operation pipe is, for example, 0.1 mm-5 mm, preferably 1-2 mm. If the approximate inner diameter is in this range, the operation pipe can have good operability. When the substantially inner diameter is below the above range, a pipe wall becomes thick to maintain the strength of the hollow pipe; as a result, a distance between the magnetic particles and the magnet increases, and a magnetic force reaching the magnetic particles becomes weak, which may cause operational problems. On the other hand, when the inner diameter of the hollow pipe exceeds the above range, an interface between the multi-layer of the gel layer and the aqueous liquid layer constituting the operation medium tends to be easily disturbed due to an impact from outside or an influence of gravity. Besides, in the disclosure, the pipe having an inner diameter of 0.1 mm or less is not excluded as long as the capillary material can withstand high-precision processing. The length in the longitudinal direction of the operation pipe is, for example, 1-30 cm, preferably 5-15 cm.

Besides, as shown in FIGS. 1B and 1C, when the sample supply portion 5 is formed in a manner that the inner diameter is wider, the approximate inner diameter of the sample supply portion 5 exceeds the above range and may be 10 mm or less, preferably 5 mm or less. It is preferable from the viewpoint of workability during sample supply that the sample supply portion has a wider inner diameter. When the wider inner diameter exceeds the above range, for example, when a plurality of operation pipes are processed at the same time, the operation pipes come into contact with each other, and integration of the device tends to decrease.

[2-3. Material of Pipe]

The material of the hollow pipe constituting the operation pipe is not particularly limited. For example, in order to reduce movement resistance when the target components and a small amount of liquid move together with the magnetic particles in the gel layer, the inner wall which is a conveyance surface is smooth and water-repellent. The material that gives such properties includes resin materials such as polyethylene, polypropylene, fluororesin (Teflon (registered trademark)), polyvinyl chloride, polystyrene, polycarbonate, acrylonitrile-butadiene-styrene copolymer (ABS resin), acrylonitrile-styrene copolymer (AS resin), acrylic resin, polyvinyl acetate, polyethylene terephthalate, cyclic polyolefin and the like. The resin materials are preferable in terms that the layer in the operation pipe is unlikely to be disturbed even if the operation pipe is dropped or bent and is highly robust. The material of the pipe may be glass if necessary for transparency, heat resistance and/or workability. The material of the sample supply portion 5, the operation pipe portion a, and the recovery pipe portion b may be the same or be different.

[2-4. Physical Properties of Hollow Pipe]

From the viewpoint of visibility during operation and from the viewpoint of optical detection in a case of measurement of absorbance, fluorescence, chemiluminescence, bioluminescence, refractive index change and the like from outside of the pipe, the material of the hollow pipe preferably has optical transparency.

The conveyance surface constituting the inner wall of the pipe is preferably a smooth surface in order to move a small amount of liquid mass containing the target components together with the magnetic particles in the gel layer; particularly, the surface roughness is preferably Ra=0.1 µm or less. For example, when a permanent magnet is brought closer to the pipe from outside and the small amount of liquid mass containing the target components moves due to the changes of the magnetic field, the magnetic particles move while being pressed against the conveyance surface, but by the conveyance surface having surface roughness of Ra=0.1 µm or less, followability of the magnetic particles to the changed magnetic field can be sufficiently provided.

[3. Filling in Operation Pipe]

[3-1. Operation Medium and Recovery Medium]

The operation pipe is at least filled with, as the operation medium, the multi-layers in which the aqueous liquid layers and the gel layers are alternately multi-layered. The uppermost layer may be a gel layer (FIG. 1A) or an aqueous liquid layer (FIGS. 1B and 1C). When the uppermost layer is an aqueous liquid layer, the layer may contain magnetic particles 6 (FIG. 1C) or may not contain the magnetic particles 6 (FIGS. 1A and 1B). The lowermost layer may be a gel layer or an aqueous liquid layer (FIGS. 1A-1C).

As shown in FIGS. 1A and 1B, when the hollow pipe constituting the operation pipe is integrally formed, all layers filled in the pipe may be in contact with each other. As shown in FIG. 1C, when the hollow pipe constituting the operation pipe consists of the operation pipe portion a and the recovery pipe portion b, the recovery pipe portion b may be filled with an aqueous liquid only as the recovery medium or may also be filled with a gel layer on the aqueous liquid layer. The gel layer 2g filled at the lowermost end of the operation pipe portion a and the aqueous liquid layer or gel layer filled at the uppermost end of the recovery pipe portion b may be in contact with each other, or may not be in contact with a layer of gas interposed therebetween (FIG. 1C).

The number and order of the layers filled in the hollow pipe are not particularly limited, and can be appropriately determined by those skilled in the art based on the number and order of the operation processes for supplying the target components. Each of the plurality of aqueous liquid layers filled in one hollow pipe preferably consists of two or more different types of aqueous liquids. As the aqueous liquid constituting each layer, liquids that construct environment necessary for each of a treatment process and a reaction process for supplying the target components can be used in order from the upper end side of the hollow pipe. Each of the plurality of gel layers filled in one hollow pipe may consist of different types of gels or may consist of the same type of gel. For example, when a heating treatment or reaction is performed in a part of the plurality of aqueous liquid layers, a gel having a high sol-gel transition point for which a gel state or a gel-sol intermediate state can be maintained even at a temperature necessary for the heating can be used in the gel layer adjacent to the aqueous liquid layer only, and a gel having a relatively low sol-gel transition point can be used in other gel layers. In addition, anyone skilled in the art can appropriately select a gel having proper characteristics corresponding to the characteristics or volume of the aqueous liquid constituting adjacent aqueous liquid layers.

The gel layer serves as a plug (gel plug) that partitions the aqueous liquid layer on both sides in the longitudinal direction of the hollow pipe in the operation pipe. As for the layer length, those skilled in the art can appropriately determine the length of the layer that functions as a plug in consideration of the inner diameter and the length of the pipe, the amount of the magnetic particles conveyed by the magnetic field applying part and the like. For example, the layer length may be 1-20 mm, preferably 3-10 mm. When the layer length is below the range, the gel layer tends to lack intensity as a plug. When the layer length is above the range, the operation pipe becomes long, and operability, durability and fillability of the operation pipe tend to deteriorate.

The aqueous liquid layer filled in the operation pipe portion a provides an environment of treatment, reaction or the like in which the sample containing the target components is supplied. As for the layer length of the aqueous liquid layer, those skilled in the art can appropriately determine the layer length that gives an aqueous liquid amount for achieving a desired treatment or reaction for the target components, in consideration of the inner diameter or length of the hollow pipe, the amount of the target components, the type of the treatment or reaction in which the target components are supplied and the like. For example, the layer length is 0.5-30 mm, preferably 3-10 mm. When the layer length is below the range, the treatment or reaction for the target components may not be sufficiently achieved, and the plug may be droplet-like and the magnetic particles may not be able to bind to the reagents. When the layer length is above the range, the aqueous liquid layer is often relatively much thicker compared with the gel layer, which may cause the same problem as the gel plug, and the interface of the multi-layer tends to be easily disturbed when the specific gravity of the aqueous liquid is larger than that of the gel.

The aqueous liquid layer filled in the recovery pipe portion b is an elution liquid of the target components, and provides an environment for liberating the target components from the magnetic particles. The aqueous liquid layer is filled in the hollow pipe so as to have a predetermined volume. Accordingly, the layer length also varies with variations in the inner diameter or length of the hollow pipe. The volume of the aqueous liquid layer can be appropriately determined by those skilled in the art in consideration of the amount of the target components, the type of the treatment or reaction in which the target components are supplied and the like so that the recovery rate of the target components recovered in the elution liquid can be accurately evaluated. For example, the volume of the aqueous liquid layer is 1 μL-1000 μL, preferably 50 μL-300 μL.

When the gel layer consists of a hydrogel, the hydrogel layer can not only function to partition the reagents but also provide an environment of the treatment or reaction or the like in which a sample containing the target components is supplied in the same manner as the aqueous liquid layer. In this case, the hydrogel layer may also be longer than the aqueous liquid layer.

[3-2. Type of Gel]

The gel layer consists of a chemically inert substance that is insoluble or poorly soluble in a liquid constituting the aqueous liquid layer when multi-layered with the aqueous liquid in the hollow pipe. Being insoluble or poor-soluble in liquid means that the solubility in the liquid at 25° C. is approximately 100 ppm or less. The chemically inert substance refers to substance that has no chemical effect on the target components and the aqueous liquid or the hydrogel during operation of the target components (that is, the treatment of the target components in the aqueous liquid or the hydrogel and transport of the target components via the gel plug). The gel in the disclosure includes both organogel and hydrogel.

[3-2-1. Organogel Gel]

Usually, the organogel can be obtained by adding a gelling agent to a water-insoluble or poorly water-soluble liquid substance for gelation.

[3-2-1-1. Water-Insoluble or Poorly Water-Soluble Liquid Substance]

As the water-insoluble or poorly water-soluble liquid substance, oil that has a solubility in water at 25° C. of approximately 100 ppm or less and that is liquid-like at room temperature (20° C.±15° C.) can be used. For example, one or a combination of two or more from a group consisting of liquid oil, ester oil, hydrocarbon oil, and silicone oil can be used.

The liquid oil includes linseed oil, camellia oil, mackerel demia nut oil, corn oil, mink oil, olive oil, avocado oil, southern power oil, castor oil, safflower oil, kyounin oil, cinnamon oil, jojoba oil, grape oil, sunflower oil, almond oil, rapeseed oil, sesame oil, wheat germ oil, rice germ oil, rice bran oil, cottonseed oil, soybean oil, peanut oil, tea seed oil, evening primrose oil, egg yolk oil, liver oil, palm oil, palm oil, palm nuclear oil, and the like.

The ester oil includes octanoic esters such as cetyl octanoate, lauric esters such as hexyl laurate, myristate esters such as isopropyl myristate and octyldodecyl myristate, palmitate esters such as octyl palmitate, stearic acid esters such as isocetyl stearate, isostearic acid esters such as isopropyl isostearate, isopalmitic acid esters such as octyl isopalmitate, oleic acid esters such as isodecyl oleate, adipic acid esters such as isopropyl adipate, sebacic acid esters such as ethyl sebacate, malate esters such as isostearyl malate, glycerin trioctanoate, glycerin triisopalmitate, and the like.

The hydrocarbon oil includes pentadecane, hexadecane, octadecane, mineral oil, liquid paraffin, and the like. The silicone oil includes dimethylpolysiloxane, methylphenylpolysiloxane and other phenyl group-containing silicone oil, methylhydrogenpolysiloxane, and the like.

[3-2-1-2. Gelling Agent]

As the gelling agent, an oil gelling agent selected from a group consisting of hydroxy fatty acid, dextrin fatty acid ester, and glycerin fatty acid ester can be used alone or in combination of two or more.

The hydroxy fatty acid is not particularly limited as long as it is a fatty acid having a hydroxyl group. Specifically, the hydroxy fatty acid includes, for example, hydroxymyristic acid, hydroxypalmitic acid, dihydroxypalmitic acid, hydroxystearic acid, dihydroxystearic acid, hydroxymargaric acid, ricinoleic acid, ricinaleic acid, linolenic acid, and the like. Among these, hydroxystearic acid, dihydroxystearic acid, and ricinoleic acid are particularly preferable. These hydroxy fatty acids may be used alone or in combination of two or more. In addition, an animal and vegetable oil fatty acid (for example, castor oil fatty acid, hydrogenated castor oil fatty acid, and the like) that is a mixture of these hydroxy fatty acids can also be used as the hydroxy fatty acid.

The dextrin fatty acid esters include, for example, dextrin myristate (trade name "Leopard MKL", manufactured by Chiba Flour Milling Co., Ltd.), dextrin palmitate (trade names "Leopard KL", "Leopard TL", both manufactured by Chiba Flour Milling Co., Ltd.), dextrin (palmitate/2-ethylhexanoate) (trade name "Leopard TT", manufactured by Chiba Flour Milling Co., Ltd.), and the like.

The glycerin fatty acid esters include glyceryl behenate, glyceryl octastearate, glyceryl eicoate, and the like, and one or more of these glycerin fatty acid esters may be used in combination. Specifically, the glycerin fatty acid esters can include trade name "TAISET 26" (manufactured by Taiyo Chemical Co., Ltd.) containing 20% of glyceryl behenate, 20% of glyceryl octastearate and 60% of hydrogenated palm oil, trade name "TAISET 50" (manufactured by Taiyo Kagaku Co., Ltd.) containing 50% of glyceryl behenate and 50% of glyceryl octastearate, and the like.

The gelling agent can be used, of which the content added to the water-insoluble or poorly water-soluble liquid substance is equivalent to, for example, 0.1-0.5 weight %, 0.5-2 weight %, or 1-5 weight % of the total weight of the liquid substance. However, the gelling agent is not limited hereto, and those skilled in the art can appropriately determine the amount to a degree at which the desired gel and sol state can be achieved.

The gelling method can be appropriately determined by those skilled in the art. Specifically, a water-insoluble or poorly water-soluble liquid substance is heated, a gelling agent is added to the heated liquid substance, the gelling agent is completely dissolved and then cooled, and thereby the liquid substance can be gelled. A heating temperature may be determined in consideration of the physical properties of the liquid substance and the gelling agent that are used. For example, the heating temperature may be preferably about 60-70° C. The gelling agent is dissolved for the liquid substance in a heated state; at this time, it is preferable that the gelling agent is dissolved while being gently mixed with the liquid substance. Cooling is preferably performed slowly. For example, the cooling can be performed over a period of about one hour to two hours. For example, the cooling can be completed when the temperature is lowered to room temperature (20° C.±15° C.) or less, preferably 4° C. An aspect to which a preferable aspect of the gelling method is applied includes, for example, an aspect in which the above-described TAISET 26 (manufactured by Taiyo Kagaku Co., Ltd.) is used.

[3-2-2. Hydrogel]

As the hydrogel, for example, the hydrogel prepared by equilibrating and swelling hydrogel materials in water or an aqueous liquid can be used, the hydrogel materials including gelatin, collagen, starch, pectin, hyaluronic acid, chitin, chitosan or alginic acid and derivatives thereof. Among the hydrogels, it is preferable to use a hydrogel prepared from gelatin. In addition, the hydrogel can also be obtained by chemically cross-linking the above hydrogel materials or processing the above hydrogel materials with the gelling agents (for example, salts of alkaline metals/alkaline earth metal such as lithium, potassium and magnesium, or salts of transition metal such as titanium, gold, silver and platinum, and silica, carbon, alumina compound or the like). These chemical cross-linking and gelling agents can be easily selected by those skilled in the art.

In particular, when the hydrogel provides an environment of treatment or reaction or the like in which a sample containing the target components is provided in the same manner as the aqueous liquid, the hydrogel is appropriately prepared by those skilled in the art so as to have a composition suitable for the treatment or reaction. The hydrogel includes, for example, a DNA hydrogel (P-gel) based on polydimethylsiloxane capable of synthesizing proteins. This hydrogel is configured by DNA which is used as a part of gel scaffold. When the target component is a substrate for protein synthesis, this hydrogel can be supplied to a reaction for obtaining a protein from the target component (the more specific aspect can be appropriately determined by those skilled in the art with reference to Nature Materials 8, 432-437 (2009), and Nature Protocols 4: 1759-1770 (2009)).

The produced protein can be recovered, for example, by using the magnetic particles having an antibody specific for the protein.

[3-2-3. Gel Characteristics]

The gel filled in the hollow pipe has a characteristic of causing the sol-gel transition at a certain temperature. The sol-gel transition point may be in a range of 25-70° C. The generation of the sol-gel transition point in this range is desirable in a reaction system that requires fluidity obtained by solification in recovery or the like. The sol-gel transition point varies depending on conditions such as the type of organogel material (oil) or hydrogel material, the type of gelling agent, the added amount of gelling agent, and the like. Accordingly, each condition is appropriately selected by those skilled in the art so as to obtain a desired sol-gel transition point.

The gel plug can be fixed in a predetermined position in the pipe by clamping the aqueous liquid in the hollow pipe from both sides in the longitudinal direction of the pipe. On the other hand, the magnetic particles can also be moved even in the gel by a magnetic field operation from outside, and can pass through the gel as a result. The reason is the thixotropic property of the gel (thixotropy). That is, the magnetic particles inside the pipe give a shearing force to the gel along the conveying surface due to the magnet movement outside the pipe, and the gel in the forward direction of the magnetic particles solates and fluidizes, and thus the magnetic particles proceed directly. Moreover, the sol released from the shearing force after the passage of the magnetic particles returns quickly to the gel state, and thus no through hole caused by the passage of the magnetic particles is formed in the gel. By utilizing this phenomenon, the object can easily move using the magnetic particles as a transporter, and thus various chemical environments in which the object is supplied can be switched in a very short time. For example, if the disclosure is used in a system consisting of a plurality of chemical reactions using a plurality of reagents, the treatment time of the object can be greatly shortened. If the property of gelation at a temperature below room temperature is utilized, even a reagent that exhibits a liquid state at that temperature can also be immobilized by being sandwiched by the gel plugs in the pipe. Therefore, the state in which the narrow pipe is filled with the liquid reagents in advance can be maintained from the time of device manufacture until the delivery to the user, and the liquid reagents can be stably supplied. Furthermore, reagent collecting and dispensing operations for each work process are not necessary, labour reduction and time saving can be achieved, and deterioration of analysis accuracy due to contamination can be prevented.

As for the physical properties of the gel, storage modulus E' of the dynamic viscoelasticity is preferably 10-100 kPa, more preferably 20-50 kPa at room temperature (20° C.±15° C.). When the storage modulus is below the range, the gel tends to lack the intensity as a gel plug. When the storage modulus is above the range, even magnetic particles having a particle size of about several micrometres tend to be easily hindered in movement. In the sol state, a kinematic viscosity may be 5 $mm^2/s$-100 $mm^2/s$, preferably 5 $mm^2/s$-50 $mm^2/s$, for example, about 20 $mm^2/s$ (50° C.).

[3-3. Type of Aqueous Liquid]

The aqueous liquid in the disclosure may be an aqueous liquid that is insoluble or poorly soluble in the gel, and may be provided in the form of water, an aqueous solution or a creamy mixture of liquids called emulsion, or a suspension in which fine particles are dispersed. The components of the aqueous liquid include all components that provide the environment of reaction and treatment in which the target components in the disclosure are supplied.

More specific examples include a liquid for liberating components to be operated in the disclosure into the aqueous liquid layer and binding or adsorbing the components to the surfaces of magnetic particles (that is, a liquid having an action of separating the target components from contaminants and promoting binding or adsorption to the surfaces of magnetic beads), a cleaning liquid for removing the contaminants coexisting with the target components, an elution liquid for separating the target components adsorbed on the magnetic particles from the magnetic particles, a reaction liquid for constructing a reaction system in which the target components are supplied, and the like. For example, when the target components are nucleic acids, the aqueous liquid includes a reagent solution (cell lysate) for destroying cells and liberating the nucleic acids, and adsorbing the nucleic acids on the silica-coated surfaces of the magnetic particles, a cleaning liquid for cleaning the magnetic particles and removing components other than the nucleic acids, an elution liquid (nucleic acid elution liquid) for separating the nucleic acids from the magnetic particles, a nucleic acid amplification reaction liquid for performing nucleic acid amplification reaction, and the like. Hereinafter, a case in which the target components are nucleic acids is illustrated, and the treatment liquid and reaction liquid for the nucleic acids and the treatment and reaction in which the nucleic acids are supplied are further described.

[3-3-1. Cell Lysate]

The cell lysate includes a buffer that contains chaotropic substances. The buffer can further include EDTA and any other chelating agent or TritonX-100 and any other surfactant. The buffer is based on, for example, Tris-HCl and any other buffer. The chaotropic substance includes guanidine hydrochloride, guanidine isothiocyanate, potassium iodide, urea and the like.

The chaotropic substance is a powerful protein denaturant, and has an action of pulling proteins such as histones bound to the nucleic acids away from the nucleic acids and promoting adsorption on the silica-coated surfaces of magnetic particles. The buffer agent can be used as an auxiliary agent that adjusts a pH environment in which the nucleic acids are easily adsorbed on the surfaces of the magnetic particles. The chaotropic substance also has an action of cell lysis (that is, an action of destroying cell membranes). However, in the action of cell lysis, a surfactant contributes more than the chaotropic substance. A chelating agent can be used as an auxiliary agent that promote the cell lysis.

A specific protocol for extracting nucleic acids from a sample containing nucleic acids can be appropriately determined by those skilled in the art. In the disclosure, since the magnetic particles are used for transporting the nucleic acids in a droplet encapsulating medium, it is preferable to adopt a method using the magnetic particles as the nucleic acid extraction method. For example, with reference to Japanese Patent Laid-Open 2-289596, a method for using magnetic particles to extract and purify nucleic acids from a sample containing nucleic acids can be implemented.

[3-3-2. Cleaning Liquid]

The cleaning liquid is preferably a solution capable of dissolving components other than the nucleic acids contained in the nucleic acid-containing sample (for example, proteins and sugars) or the reagents and other components used for other treatments performed in advance such as nucleic acid extraction while the nucleic acids are adsorbed on the surfaces of the magnetic particles. Specifically, the cleaning liquid includes high salt concentration aqueous solutions such as sodium chloride, potassium chloride and ammonium sulfate, alcohol aqueous solutions such as ethanol and isopropanol, and the like. The cleaning of the nucleic acids is cleaning of the magnetic particles on which the nucleic acids are adsorbed. A specific protocol for this cleaning can be appropriately determined by those skilled in the art. In addition, the number of times of the cleaning of the magnetic particles on which the nucleic acid are adsorbed can be appropriately selected by those skilled in the art to a degree that undesired inhibition does not occur during the nucleic acid amplification reaction. In addition, when the effect of inhibitory components can be ignored from the same viewpoint, the cleaning process can also be omitted. The aqueous liquid layer consisting of the cleaning liquid is prepared at least as many times as the number of times of the cleaning.

[3-3-3. Nucleic Acid Elution Liquid]

A buffer containing water, salt or the like can be used as the nucleic acid elution liquid. Specifically, a Tris buffer, a phosphate buffer, distilled water and the like can be used. A specific method for separating the nucleic acids from the magnetic particles on which the nucleic acids are absorbed and eluting the nucleic acids into the elution liquid can also be determined appropriately by those skilled in the art.

[3-3-4. Nucleic Acid Amplification Reaction Liquid]

In the nucleic acid amplification reaction liquid of the disclosure, various elements usually used in the nucleic acid amplification reaction at least include nucleic acids containing base sequences to be amplified and magnetic particles that adsorb the nucleic acids on the surfaces thereof.

Since the nucleic acid amplification reaction is not particularly limited as described later, the various elements used in the nucleic acid amplification reaction can be appropriately determined by those skilled in the art based on the known nucleic acid amplification method illustrated later and the like. Usually, the various elements include salts such as $MgCl_2$, KCl, primers, deoxyribonucleotides, nucleic acid synthases, and pH buffers. In addition, the above salts may be appropriately changed into other salts to use. In addition, substances for reducing non-specific priming, such as dimethyl sulfoxide, betaine, glycerol and the like, may be further added.

In addition to the above components, a blocking agent can be added to the nucleic acid amplification reaction liquid in the disclosure. The blocking agent can be used for the purpose of preventing deactivation of DNA polymerase due to adsorption to the inner wall of a reaction vessel, the surfaces of the magnetic particles or the like. Specific examples of blocking agents include bovine serum albumin (that is, BSA), other albumins, gelatin (that is, denatured collagen), proteins such as casein and polylysine, peptides (both natural and synthetic), ficoll, polyvinyl pyrrolidone, polyethylene glycol, and the like.

The nucleic acid amplification reaction of the disclosure is not particularly limited, and for example, PCR method (U.S. Pat. No. 4,683,195, No. 4683202, No. 4800159, and No. 4965188), LCR method (U.S. Pat. No. 5,494,810), Qβ method (U.S. Pat. No. 4,786,600), NASBA method (U.S. Pat. No. 5,409,818), LAMP method (U.S. Pat. No. 3,313,358), SDA method (U.S. Pat. No. 5,455,166), RCA method (U.S. Pat. No. 5,354,688), ICAN method (JP Patent No. 3433929), TAS method (JP Patent No. 2843586), and the like can be used. In addition, a reverse transcription (RT) reaction can also be performed prior to the above reaction. Those skilled in the art can appropriately select the composition of reaction liquid and the reaction temperature necessary for these nucleic acid amplification reactions.

Besides, when the nucleic acid amplification reaction is further performed after the reverse transcription (RT) reaction, for example, when RT-PCR is performed, the RT reaction liquid layer can be multi-layered on the PCR reaction liquid layer via the gel layer in the recovery portion B (for example, as illustrated in FIGS. 4A to 4H).

In a real-time nucleic acid amplification method, fluorescence detection can be performed on amplification products by a fluorescent dye capable of binding to a double-stranded DNA or by a probe labelled with the fluorescent dye. Detection methods in the real-time nucleic acid amplification method include the following methods.

For example, when it is possible to amplify a desired target only by a highly specific primer, an intercalator method using SYBR (registered trademark) GREEN I or the like is used. An intercalator that emits fluorescence by binding to a double-stranded DNA binds to the double-stranded DNA synthesized by the nucleic acid amplification reaction, and emits fluorescence of a specific wavelength by irradiation of an excitation light. By detecting this fluorescence, the generation amount of the amplification products can be monitored. This method does not require design and synthesis of a fluorescently labelled probe specific to the target, and can be conveniently utilized in measurement of various targets.

In addition, when it is necessary to distinguish and detect similar sequences or when SNPs are typed, a fluorescently labelled probe method is used. As an example, there is a TaqMan (registered trademark) probe method for using an oligonucleotide in which 5' terminal is modified with a fluorescent substance and 3' terminal is modified with a quencher substance as a probe. The TaqMan probe is specifically hybridized to a template DNA in an annealing step, but the quencher is present on the probe and thus fluorescence emission is suppressed even when the excitation light is irradiated. In an extension reaction step, when the TaqMan probe hybridized to the template is decomposed by 5'→3' exonuclease activity of the TaqDNA polymerase, the fluorescent dye is liberated from the probe, the suppression caused by the quencher is released and the fluorescence is emitted. By measuring the fluorescence intensity, the generation amount of amplification products can be monitored.

The principle of quantifying DNA in the real-time PCR by this method is described below. First, a serially diluted standard sample of known concentration is used as the template to perform the PCR. Then, the number of cycles (threshold cycle; Ct value) reaching a certain amount of amplification products is obtained. A calibration curve is created by plotting the Ct value on the horizontal axis and an initial DNA amount on the vertical axis. For a sample of unknown concentration, the PCR reaction is also performed in the same conditions to obtain the Ct value. From this value and the above-described calibration curve, a desired DNA amount in the sample can be measured.

Furthermore, in an intercalator method, when the temperature of the liquid after the PCR reaction containing a fluorescent dye is gradually increased from 40° C. to about 95° C. and the fluorescence intensity is continuously monitored, a melting curve of the amplification products can be obtained. The double-stranded DNA generated by the nucleic acid amplification reaction has a unique Tm value depending on the length of DNA and the base sequence thereof. In other words, when the temperature of droplets containing the DNA to which the fluorescent dye is bound is gradually increased, a temperature at which the fluorescence intensity rapidly decreases is observed. When the change amount of change in fluorescence intensity is examined, the temperature peak substantially coincides with the Tm value defined by the base sequence and the length. As a result, for example, data which is not the target gene and observed when a primer dimer occurs (that is, false positive data) can be excluded from data regarded as positives. In a genetic testing, non-specific reactions also often occur due to contaminants in the sample, so it is important to eliminate the false positives. Accordingly, a determination can also be performed on whether the generated amplification products are unique to the target genes.

[3-3-5. Other Aqueous Liquids]

For any reaction and treatment other than the above reaction, the composition of each aqueous liquid can be easily determined by those skilled in the art. In addition, even when the target component is a component other than the above nucleic acid, the composition of each aqueous liquid can be easily determined by those skilled in the art.

[4. Manufacturing Method of Operation Pipe]

As a manufacturing method of operation pipe, the following two methods are described according to an aspect in which a hollow pipe to be filled with multilayers being an operation medium is prepared.

[4-1. A Case in which One Hollow Pipe is Prepared for Manufacturing One Operation Pipe]

The case in which this creation method is performed may be a case in which the hollow pipe is prepared in a state of being integrally formed, or a case in which the pipe is configured by the operation pipe portion a and the recovery pipe portion b and prepared in a state that the pipe portion a and the pipe portion b are connected. In one hollow pipe, the necessary aqueous liquid and gel are filled so as to be alternately multi-layered in a necessary order from the lower closed end and thereby the operation medium can be formed, and the operation pipe can be manufactured. In this case, after a predetermined amount of volume of the aqueous liquid in contact with the lower closed end is filled, filling is performed while the vertical thickness of the aqueous liquid layer and the gel layer multi-layered on the aqueous liquid layer, that is, the length in the longitudinal direction of the hollow pipe is specified. When the hollow pipe is configured by the operation pipe portion a and the recovery pipe portion b, first, the recovery unit B is completed when filling of the recovery medium necessary for constituting the recovery portion B, that is, filling of the aqueous liquid having a predetermined volume or formation of multilayers of the aqueous liquid having a predetermined volume and the gel layer having a predetermined thickness is completed. Furthermore, the operation portion A is completed by filling of the operation medium necessary for constituting the operation portion A, that is, formation of multilayers of the aqueous liquid layer and the gel layer that have a predetermined thickness is completed. A more specific method for forming multilayers by alternately multi-layering the aqueous liquid and the gel can be appropriately performed by those skilled in the art according to the multi-layer method in a case of 4-2 described later. Besides, after necessary aqueous liquid and/or gel are/is filled, the sample supply portion that is an upper open end may be appropriately closed.

[4-2. A Case in which a Plurality of Hollow Pipes are Prepared for Manufacturing One Operation Pipe]

The case in which this creation method is performed may be a case in which the pipe is configured by the operation pipe portion a and the recovery pipe portion b and prepared in a state that the pipe portion a is independent from the pipe portion b. In this case, the operation portion A and the recovery portion B are separately manufactured by filling necessary aqueous liquid and/or gel in each of the pipe portion a and the pipe portion b, and the manufactured operation portion A and recovery portion B are connected to each other, and thereby the operation pipe can be manufactured.

Figure 2A:
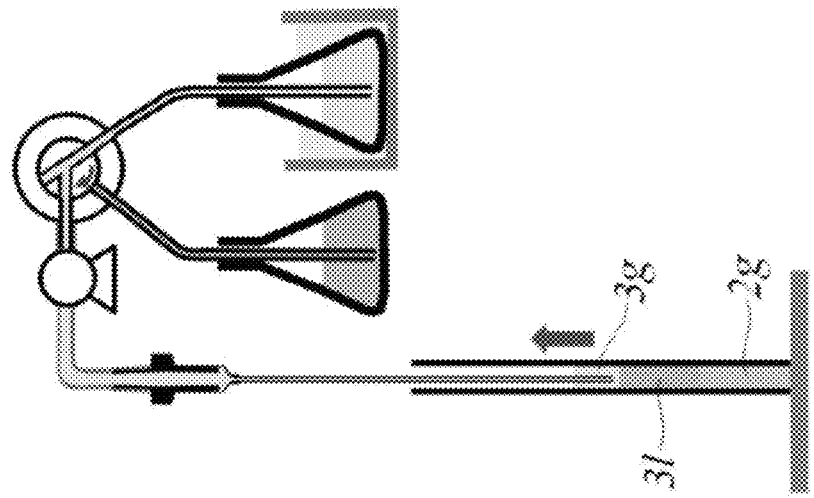
FIGS. 2A to 2C show an example of a manufacturing method of the operation pipe of the disclosure.
Figure 2B:
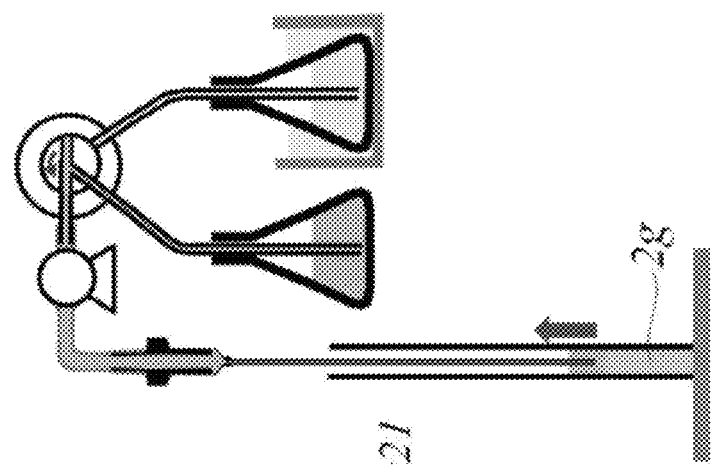
Figure 2C:
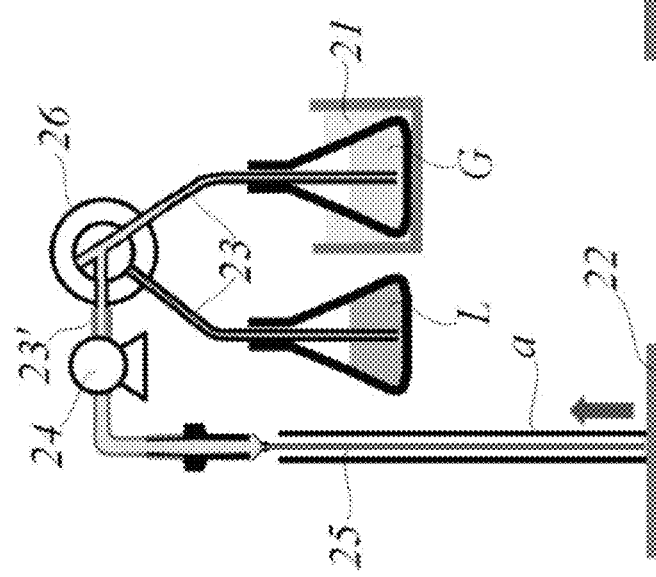

An outline of the manufacturing method of the operation portion A is schematically shown in FIGS. 2A to 2C. An aqueous liquid L (for example, a cleaning liquid) constituting the aqueous liquid layer is filled in the container, and a gel G constituting the gel layer is filled in another container in a sol state. In FIGS. 2A to 2C, the sol state is maintained by heating in a constant temperature bath 21 of 70° C. for example. The lower open end of the pipe portion a is prepared in a state of being closed by being pressed against a holding mat 22.

A system for feeding liquid into the pipe portion a includes tubes 23 and 23' that respectively extend from the container filled with the aqueous liquid L and the sol-gel G and feed the aqueous liquid L or the sol-gel G, a liquid feeding part 24 (peristaltic pump in FIGS. 2A to 2C) to which the tube 23' is connected, and a needle 25 for filling the pipe portion a with liquid substances that are fed by the liquid feeding part. The needle 25 preferably has a length enough to reach the bottommost portion of the pipe portion a by being inserted into the pipe portion a.

In FIGS. 2A to 2C, the tube 23 extending from the container filled with the aqueous liquid L and the tube 23' extending from the container containing the sol-gel G are connected to a switching valve 26. In this case, by switching the valve 26, different liquid substances (the aqueous liquid L and the sol-gel G) can be respectively fed to the same tube 23' and the same needle 25. This aspect is preferably used when the inner diameter of the pipe portion a is relatively small because only one needle is inserted into the pipe portion a.

On the other hand, all liquid feeding paths from the container to the needle may be made independent without using the switching valve 26. For example, when the same operation portion A as FIGS. 2A to 2C is manufactured, two liquid feeding paths can be formed, one formed by a tube extending from the container filled with the aqueous liquid and a needle connected to the tube and the other formed by a tube extending from the container containing the sol-gel and a needle connected to the tube. In this aspect, the operation pipe is preferably used when the inner diameter of the pipe portion a is relatively large because two needles can be inserted into the pipe portion a.

As shown in order in FIGS. 2A-2C, the sol-gel G and the aqueous liquid L are alternately fed and filled into the pipe portion a in order from the sol-gel G. The leading end of the needle 25 is raised as the liquid level in the pipe portion a rises. When the aqueous liquid L is multi-layered as shown in FIG. 2B after the sol-gel is filled, the previously filled sol-gel may be completely gelled or may not be completely gelled. Usually, the liquid substances that are fed from the container filled with the sol-gel G may be in an intermediate state of gel-sol with increased viscoelasticity so as to be away from heat source (the constant temperature bath 21 in FIGS. 2A to 2C) when discharged into the pipe portion a from the needle 25 inserted into the pipe portion a. Therefore, when the aqueous liquid is multi-layered, even if the previous layer 2 is not completely gelled, the contact resistance of the gel 2g against the inner wall of the pipe portion a works, and the gel 2g having a low specific gravity does not float up. Accordingly, by alternately feeding the sol-gel G and the aqueous liquid L into the pipe portion a, the required number of layers can be formed and the operation portion A can be obtained. Besides, during the filling, the aqueous liquid and the gel are filled with a prescribed thickness based on the thickness of the hollow pipe in the vertical direction.

The recovery portion B can be obtained by filling necessary aqueous liquid or gel. Alternatively, the recovery portion B can be obtained by forming a single layer of the aqueous liquid layer or multilayers of the aqueous liquid layer and the gel layer in an appropriate and necessary order in the same manner as described above except that a holding mat is not used. During the filling, the aqueous liquid is filled with a predetermined amount on the basis of volume, and the gel is filled with a prescribed thickness on the basis of the thickness of the hollow pipe in the vertical direction.

The operation portion A and the recovery portion B obtained as described above are connected to each other. The operation portion A may be connected to the recovery portion B in a state that the pipe portion a is inclined and the holding mat is removed and inclined or overturned so that the contents of the operation portion A do not slide down. As a form of connection, the pipe portion a and the pipe portion b may be wound around a tape or the like, or the pipe portion a and the pipe portion b in which connection portions that can be connected to each other are respectively formed may be used to connect both of the connection portions.

Besides, after necessary aqueous liquid and/or gel are/is filled, the sample supply portion which is an upper open end of the operation pipe portion a may be appropriately closed. The timing for closing may be after the operation portion A is manufactured and before the operation portion A and the recovery portion B are connected, or after the operation portion A and the recovery portion B are connected.

[5. Magnetic Particles]

The magnetic particles are used to move, by the variations of the magnetic field from outside of the operation pipe, the target components in the operation pipe by being accompanied by a small amount of accompanying liquid mass. The magnetic particles intended to enable separation, recovery and purification of specific components by the above movement usually have chemical functional groups on the surfaces thereof. The magnetic particles may not be filled in the operation pipe in advance (FIGS. 1A and 1B) or may be filled in advance (FIG. 1C, FIGS. 3A to 3O and FIGS. 4A to 4H). When filled in the operation pipe in advance, the magnetic particles can be added to the aqueous liquid constituting the uppermost layer. When the magnetic particles are not added to the operation pipe in advance, the magnetic particles are also supplied to the operation pipe when the sample having the target components is supplied to the operation pipe.

The magnetic particles are not particularly limited as long as they are particles that respond to magnetism, and include, for example, particles having a magnetic body such as magnetite, γ-iron oxide, manganese zinc ferrite or the like. In addition, the magnetic particles have a chemical structure that specifically binds to the target components supplied to the above treatment or reaction, and may have a surface containing, for example, amino group, carboxyl group, epoxy group, avidin, biotin, digoxigenin, protein A, protein G, complex metal ion or antibody, or may have a surface that specifically binds to the target components by an electrostatic force or a van der Waals force. Accordingly, the target components supplied to the reaction or treatment can be selectively adsorbed to the magnetic particles. Hydrophilic groups on the surfaces of the magnetic particles include hydroxyl groups, amino groups, carboxyl groups, phosphoric acid groups, sulfonic acid groups, and the like.

In addition to the above particles, the magnetic particles can further include various elements appropriately selected by those skilled in the art. For example, specific forms of the magnetic particles having hydrophilic groups on the surfaces preferably include particles consisting of mixture of magnetic bodies and silica and/or an anion exchange resin, magnetic particles of which the surfaces are covered by the silica and/or the anion exchange resin, magnetic particles of which the surfaces are covered by gold and which have hydrophilic groups via mercapto groups, gold particles containing magnetic bodies and having hydrophilic groups via mercapto groups on the surfaces, and the like.

As for the size of the magnetic particles having hydrophilic groups on the surfaces, the average particle size is about 0.1 μm-500 μm. When the average particle size is small, the magnetic particles are easy to exist in a dispersed state when released from the magnetic field in the aqueous liquid layer. An example of commercially available magnetic particles includes Magnetic Beads which are component reagents of Plasmid DNA Purification Kit MagExtractor-Plasmid-sold by Toyo Tamotsu and are silica-coated for nucleic acid extraction. When sold as a kit of component reagents in this way, a product stock solution containing magnetic particles contains a preservative solution and the like, and thus is preferably cleaned by being suspended in pure water (for example, about 10 times of the amount). The cleaning can be performed by suspending in pure water and then removing the supernatant by centrifugation or aggregation using a magnet, and can be performed by repeating the suspension and supernatant removal. Besides, the magnetic field applying part for giving magnetic field variations to move the magnetic particles is described in detail in item 8 below.

[6. Method for Operating Target Components in Pipe]

The operations of the target components in the operation pipe are shown in FIGS. 3A-3O and FIGS. 4A-4H. Hereinafter, description will be given with reference to FIGS. 3A to 3O and FIGS. 4A-4H.

[6-1. Sample Supply to Operation Pipe]

When the operation pipe is used, a sample 32 containing the target components is supplied from a reagent supply port 5 (FIG. 3B and FIG. 4B). Usually, the sample is supplied in the form of liquid. The sample supply may be performed manually by a syringe or the like, or may be automatically controlled by a dispenser using a pipetter or the like. The sample supply is performed in a state that the operation pipe is held up by an appropriate holding part (not shown; the holding part for holding the operation pipe is described in detail in item 7 below).

In the uppermost layer in the operation pipe, an aqueous liquid mixture 33 that contains the sample 32 containing the target components, the magnetic particles 6 and the aqueous liquid are obtained. More specifically, the aqueous liquid mixture can be obtained as follows. For example, when the uppermost layer filled in the operation pipe consists of an aqueous liquid, the sample may be supplied into the operation pipe together with the magnetic particles, or the sample may be supplied into the operation pipe together with the aqueous liquid and suspended magnetic particles. In this way, the aqueous liquid mixture can be obtained from the aqueous liquid in the uppermost layer. In addition, for example, when the uppermost layer filled in the operation pipe consists of an aqueous liquid containing magnetic particles (the case illustrated in FIGS. 3A to 3O and 4A to 4H is applicable), the sample only may be supplied into the operation pipe, or the sample may be supplied into the operation pipe together with the aqueous liquid. In this way, the aqueous liquid mixture can be obtained from the aqueous liquid containing magnetic particles in the uppermost layer. Furthermore, for example, when the uppermost layer filled in the operation pipe consists of gel, the sample may be supplied into the operation pipe together with the aqueous liquid and the magnetic particles. In this way, the aqueous liquid mixture can be newly formed as the uppermost layer on the gel layer.

[6-2. Operations in Operation Pipe]

The operation pipe in which the sample is supplied and the aqueous liquid mixture containing the sample and magnetic particles is prepared in the uppermost layer is held up on the holding part and directly set on a device or set on a device under the condition of being transferred to a dedicated holding part in the device. In the device, a magnetic field is generated by bringing a magnetic field applying part (for example, a cylindrical neodymium magnet having a diameter of 1 mm-5 mm and a length of 5 mm-30 mm) 31 from outside close to an operation pipe 1, and magnetic particles 6 dispersed in an aqueous liquid mixture layer $3l_1$ are aggregated together with the target components (FIG. 3C and FIG. 4C). At this time, unnecessary components contained in the aqueous liquid mixture layer $3l_1$ can be also aggregated together. By moving the magnetic field applying part 31 downward at a speed of 0.5 mm-10 mm per second, the magnetic particles accompanied by the target components are transported from the aqueous liquid mixture layer $3l_1$ via a gel layer $3g_1$ located below and in contact with the aqueous liquid mixture layer $3l_1$ (see FIG. 3D and FIG. 4D) to an aqueous liquid layer $3l_2$ located below and in contact with the gel layer $3g_1$ (FIG. 3E and FIG. 4E). Besides, since the magnetic particles passing through the gel layer $3g_1$ are thinly coated on the aqueous liquid mixture of the aqueous liquid mixture layer $3l_1$ supplied before passage, the magnetic particles are accompanied by concomitants in addition to the target components and the concentration is low. The magnetic particles are further transported to the aqueous liquid layer $3l_2$. The size and movement speed of the magnet are appropriately determined by those skilled in the art corresponding to the amount of the magnetic particles, the inner and outer diameters of the operation pipe, the state of the gel plug, and the like.

Furthermore, transportation from the aqueous liquid layer $3l_2$ to another aqueous liquid layer via the gel layer is repeated by the magnetic field applying part 31 as necessary. "Repeating as necessary" means that, as a general rule, the transport operation may be performed as many as the number of times corresponding to the layer number by moving the magnetic particles only in one direction from the top to the bottom (FIGS. 3E-3N and FIGS. 4E-4H), or the transport operation may be performed for the number of times above the number corresponding to the layer number by moving the magnetic particles not only in one direction from the top to the bottom but also from the bottom back to the top as appropriate. That is, other aqueous liquid layers of the transport destination may be present above or below the aqueous liquid layer of the transport source. By repeating this transport operation, most of the contaminants transported by the magnetic particles together with the target components are removed. Although the magnetic particles accompanying the target components are accompanied by a very small amount of cleaning liquid, the target components on the surfaces of the particles are purified to such a degree that a subsequent analysis process and the like are not interfered. Accordingly, the purification of the target components can be performed very efficiently by the magnetic field operation only.

In addition, in the aqueous liquid layer, from the viewpoint of improving the processing efficiency, it is preferable to operate so that the magnetic particles with the target components (specifically, including target components accompanied by unnecessary components and target components from which unnecessary components are removed) can be sufficiently brought into contact with the aqueous liquid. As one of the methods for more efficiently performing this operation, there is a method in which the magnetic field applying part is moved up and down in a state that the magnetic particles are aggregated due to application of the magnetic field in the aqueous liquid layer. Other methods include the method in which the magnetic particles that are aggregated due to the application of the magnetic field are naturally diffused in the aqueous liquid layer by opening the magnetic field from the magnetic particles that are subjected to the application of the magnetic field using the magnetic field applying part.

As a specific example, as shown in FIG. 3E, the magnetic field is blocked or attenuated by temporarily bringing the magnetic field applying part 31 away from the operation pipe 1, and the magnetic particles are dispersed in a cleaning liquid layer $3l_2$. In this way, the target components adsorbed on the magnetic particles are cleaned by being sufficiently exposed in the cleaning liquid $3l_2$ together with the accompanying components. As shown in FIG. 3F, the magnetic field applying part 31 is brought closer to the operation pipe 1 again and thereby the magnetic particles are aggregated together with the target components and are in a transportable state. By further moving the magnetic field applying part 31 downward, the magnetic particles are transported to the gel layer $3g_2$ just below as shown in FIG. 3G. In the magnetic particles and the target components in the gel layer $3g_2$ in FIG. 3G, compared with a case of the magnetic layer particles and the target components in the gel layer $3g_1$ in FIG. 3D, some or most of the accompanying components are removed by the cleaning in FIG. 3E.

After separating a target substance from the magnetic particles in the layer filled in the recovery portion B, the magnetic particles from which the target substance is separated are moved from the layer in which the target substance is separated to another layer (for example, FIGS. 3N-3O), and thereby the target substance can be recovered in a state of being eluted from the magnetic particles in the recovery portion.

[6-3. Nucleic Acid Extraction]

For example, when the magnetic particle surfaces are coated with silica, as shown in FIGS. 3A to 3O, the biological sample is supplied to a cell lysate $3l_1$ containing a surfactant and a chaotropic salt such as guanidine thiocyanate, and thereby the nucleic acids are liberated from the cells (FIG. 3B). The liberated nucleic acids can be specifically adsorbed on the silica surfaces of the particles. The adsorbed nucleic acids contain reaction inhibition components in this state and thus cannot be utilized as a template for gene amplification reaction. Therefore, the magnetic particles are cleaned by the cleaning liquid $3l_2$ while the nucleic acids are adsorbed on the surfaces. At this time, in order to prevent a large amount of reaction inhibition components from being introduced into the cleaning liquid, the magnetic particles 6 are collected by a magnet 31 (FIG. 3C), and are made to pass through a gel plug $3g_1$ that separates the cell lysate $3l_1$ and the cleaning liquid $3l_2$ (FIG. 3D). The magnetic particles can reach the cleaning liquid $3l_2$ with little liquid fraction when passing through the gel plug $3g_1$ (FIG. 3E). Therefore, the cleaning of the magnetic particles can be implemented with high efficiency. By further repeating passage through gel plugs ($3g_2$, $3g_3$) and transport to cleaning liquids ($3l_3$, $3l_4$) of the magnetic particles (FIGS. 3F-3K), purity of the nucleic acids can be increased. The nucleic acids purified in a state of being adsorbed on the magnetic particle surfaces are collected again by a magnet (FIG. 3L), made to pass through a gel plug $2g$ (FIG. 3M), and transported into an elution liquid 4 (FIG. 3N). In the elution liquid 4, the nucleic acids are separated from the magnetic particles and eluted in the elution liquid. When it is not desired to mix the magnetic particles, the magnetic particles from which the nucleic acids are eluted are retained in the gel plug $2g$ again, and the eluted purified nucleic acids remain in the recovery portion B (FIG. 3O). The nucleic acids obtained in this way are useful as template nucleic acids that can be analyzed by nucleic acid amplification reaction. The obtained nucleic acids can be used for the next operation (process for performing analysis by nucleic acid amplification reaction) by removing the recovery portion B of the operation pipe from the operation portion A.

[6-4. Nucleic Acid Synthesis and Analysis]

As shown in FIGS. 4A to 4H, when the operation pipe is used in which the pipe portion a of the operation portion A and the pipe portion b of the recovery portion B are formed integrally, and which has the operation portion A similar to the operation portion in FIGS. 3A to 3O and the recovery portion B filled with a RT reaction liquid $4l_1$ and a PCR reaction liquid $4l_2$ separated by a gel plug $4g$, after the same operation (FIGS. 4B-4F) as that in FIGS. 3B-3M is performed, the magnetic particles 6 are transported to the RT reaction liquid $4l_1$ while adsorbing the purified nucleic acid (RNA) and the RT reaction is performed (FIG. 4H). After completion of the RT reaction, the magnetic particles also adsorb the DNA (which is a template for PCR reaction) obtained by the RT reaction, pass through the gel plug $4g$ to be transported to the PCR reaction liquid $4l_2$, and the PCR reaction is performed (FIG. 4H). The PCR product can be analyzed by a real-time detection method using a fluorescent dye or a fluorescence detection method using an endpoint detection method. Besides, in FIGS. 4A to 4H, 42 and 43 schematically show temperature control functions. A more specific example of the temperature control function of 42 is shown in the subsequent item 8-2-6, and a more specific example of the temperature control function of 43 is shown in the subsequent item 7-3.

Figure 5:
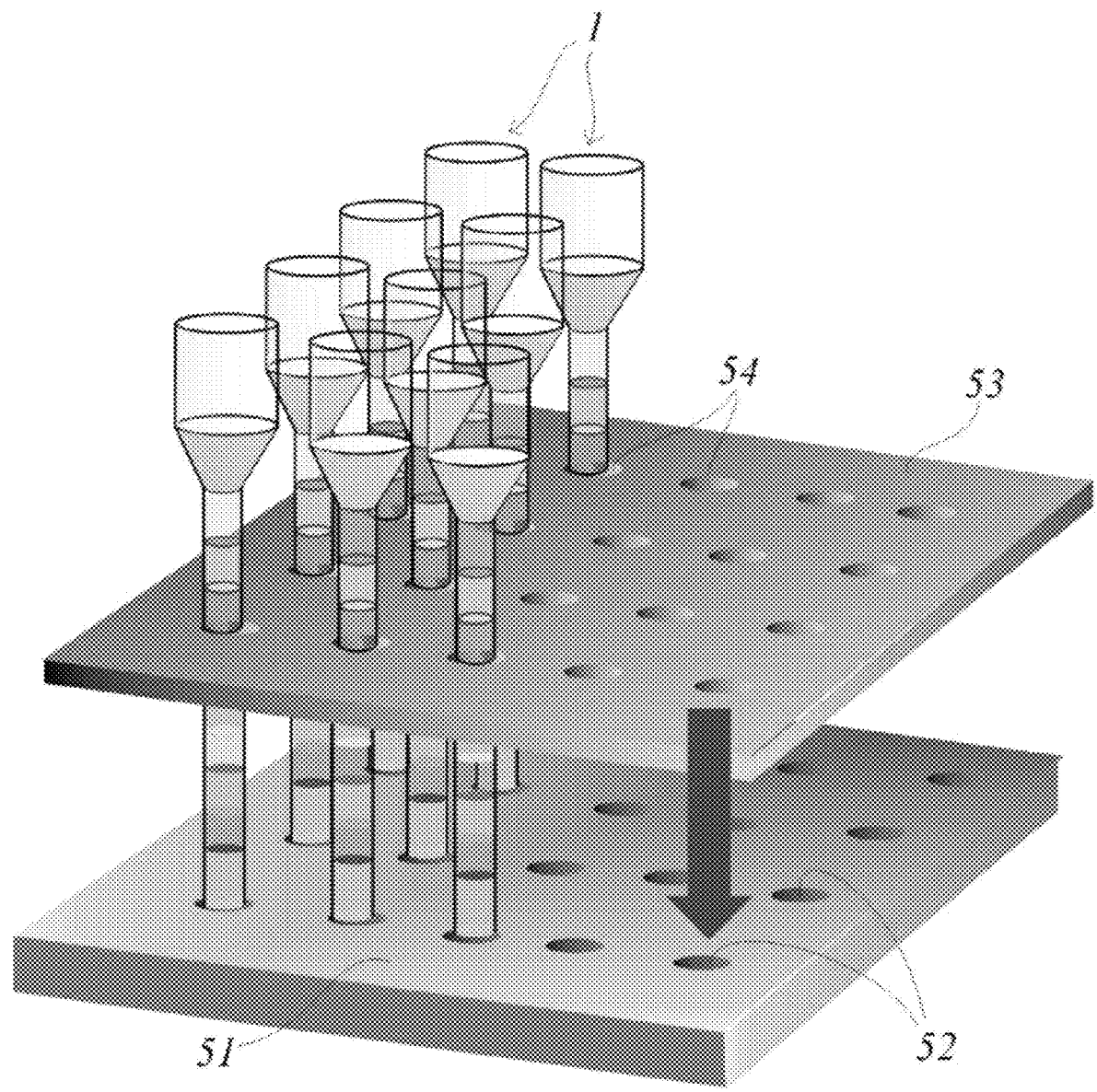
FIG. 5 is a perspective view showing an example of a device that enables a simultaneous operation in the operation pipe by using a plurality of operation pipes of the disclosure to make multiple channels.

When the above operation is performed simultaneously in a plurality of operation pipes, multiple channels can be made as shown in FIG. 5. The device illustrated in FIG. 5 has a simple configuration in which a magnetic field applying part (movable magnet plate 53) having a magnet moving mechanism and a holding substrate with temperature control function (temperature control block 51) are main units. Each configuration is described in items 7 and 8 described later.

[6-5. Protein Synthesis, Separation and Analysis]

[6-5-1. Protein Synthesis Using Hydrogel (P-Gel)]

A cell-free protein synthesis system on the basis of polydimethylsiloxane is published in the aforementioned reference literature (Nature materials 8, 432-437, 2009). The cell-free protein synthesis system is performed in a general-purpose sample tube, but this cell-free protein synthesis system can also be constructed in the operation pipe of the disclosure.

[6-5-2. Analysis Using Interaction Between Target Protein and Other Proteins]

A separation and recovery part of protein already exists as a commercially available purification kit, the separation and recovery part utilizing an antigen-antibody reaction of a protein and an antibody (also a protein) that is manufactured using the protein as a target. The separation and recovery are implemented by a process using a general-purpose tube and a centrifuge. In the cell-free protein system described above, a spin column is also used separately from the sample tube for separation of the synthesized protein. In the disclosure, by adopting magnetic particles in which the antibody of the target protein is immobilized on the surface, the target protein can be separated and acquired in one operation pipe without moving the target protein between different devices.

[6-5-3. Mass Spectrometry in a State that Protein is Adsorbed on Magnetic Particles]

A method for adsorbing a separately prepared protein to be subjected to mass spectrometry to magnetic particles coated with titanium oxide on the surface, mixing the protein with a matrix in the above state, and analyzing the protein with a mass spectrometer is described in the reference literature (Analytical Chemistry, 77, 5912-5919, 2005). In the disclosure, the preparation of the protein to be subjected to mass spectrometry and the adsorption to the magnetic particles can be performed in one operation pipe.

[7. Holding Part]

The operation pipe is usually installed in a substantially vertical shape (that is, in a hold-up state) so that the sample supply portion which is an opening portion is on the upper side during use. An appropriate holding part can be used for installation. In addition, the same holding part may be used during sample supply and during operation of the target components, or different holding parts may be used. When different holding parts are used during sample supply and during operation of the target components, the transfer of the operation pipe between the holding parts may be manually performed or be automated.

[7-1. Holding Form]

The holding part is not particularly limited as long as it can be held in a substantially vertical state (that is, in a hold-up state) so that the sample supply portion which is an opening portion of the operation pipe is generally on the upper side. The holding part includes, for example, a rack which is configured by combining one or two or more holding members formed with holding holes that can hold the closed end of the operation pipe by piercing of the closed end, or configured by assembling linear members in a lattice shape to form lattice holes as holding holes, but the disclosure is not limited hereto. In the former case, the holding hole formed in the holding member may penetrate or may not penetrate the holding member. The inner diameter of the holding hole is determined based on the outer diameter of the operation pipe to be held. Among the holding members, the one that holds the closed end of the operation pipe is described as a holding substrate. In the holding substrate, the holding hole can be formed so that the closed end of the holding portion B does not penetrate the holding substrate (that is, the holding hole itself does not penetrate the holding substrate). The depth of the holding hole is appropriately determined based on the range to be held in the operation pipe.

[7-2. Holding of a Plurality of Operation Pipes]

Since the operation pipe of the disclosure is elongated and has an extremely small installation area of one pipe during hold-up, a plurality of operation pipes can be held up and installed in a concentrated state even with a small installation area. As a result, the plurality of operation pipes can be operated simultaneously. That is, a multi-channel operation can be achieved.

An example of this form is shown in FIG. 5. In the device of FIG. 5, up to 20 operation pipes can be processed simultaneously. More operation pipes can also be processed depending on the device specifications. For example, if there is an installation area as large as a standard 96-well plate, up to 96 operation pipes can be held up, and thereby up to 96 specimens can be processed simultaneously. In addition, since the operation pipes are independent from each other, in the above example, the number of operation pipes can be arbitrarily adjusted corresponding to the number of specimens. This form is particularly useful in POCT (Point Of Care Testing) applications in which the number of specimens is small and the number is also not constant.

When a plurality of operation pipes are held up and installed, for example, as shown by 51 in FIG. 5, a plurality of holding holes 52 can be formed in the holding substrate. The holding holes differ depending on a form of densifying the operation pipes, and can be formed, for example, in an array shape (that is, formed one-dimensionally in a row) or in a matrix shape (that is, formed two-dimensionally) as shown in FIG. 5. An interval between the holding holes 52 can be appropriately determined based on the density of the operation pipes. When the operation pipe held by the holding hole 52 has a larger inner diameter in the sample supply portion, the interval between the holding holes 52 can be appropriately determined based on the outer diameter of the sample supply portion.

[7-3. Temperature Control Function]

The holding part may have a temperature control function. More specifically, the holding part may have a temperature control function in a portion that holds at least a part of the recovery portion B. For example, in FIGS. 4A to 4H, the temperature control function is schematically shown as 43. More specifically, when the holding substrate holds the closed end of the recovery portion B in the holding hole, the holding substrate can have the temperature control function in the portion for holding. For example, a holding substrate 51 shown in FIG. 5 holds the closed end of the recovery portion B in a holding hole 52, but the holding substrate 51 itself may be formed of a temperature control block. The temperature control function makes it possible to perform a treatment or reaction requiring temperature control in the aqueous liquid filled at least at the lower end of the recovery portion B. In the disclosure, this form is preferably used, for example, when the nucleic acid amplification reaction is performed in the recovery portion B.

[7-4. Optical Detection Port]

Figure 7A:
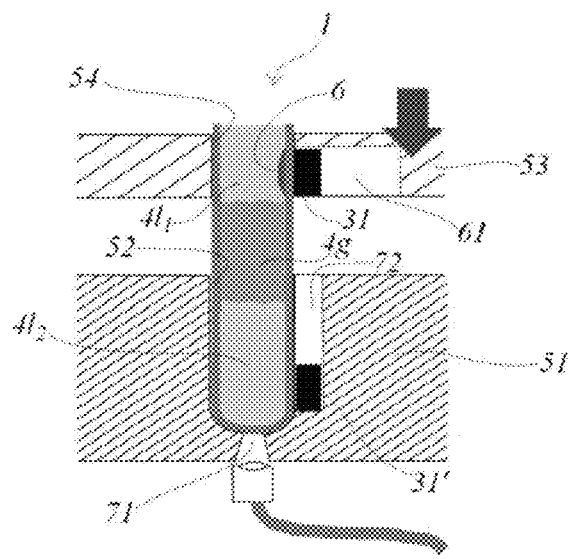
FIG. 7A is a longitudinal-sectional view of the variation example of the magnetic field applying part (movable magnet plate) shown in FIG. 5.
Figure 7B:
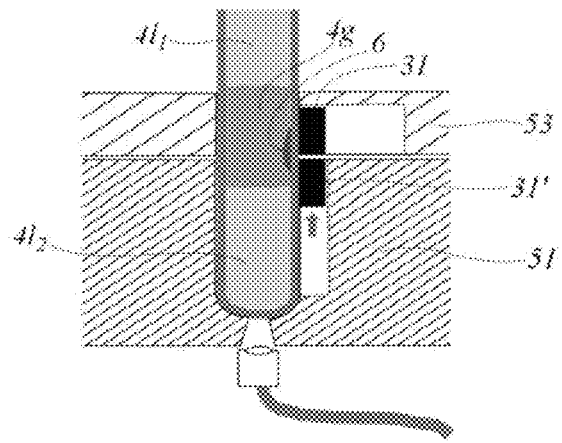
FIG. 7B is a longitudinal-sectional view of a variation example of a holding part (holding substrate)
Figure 7C:
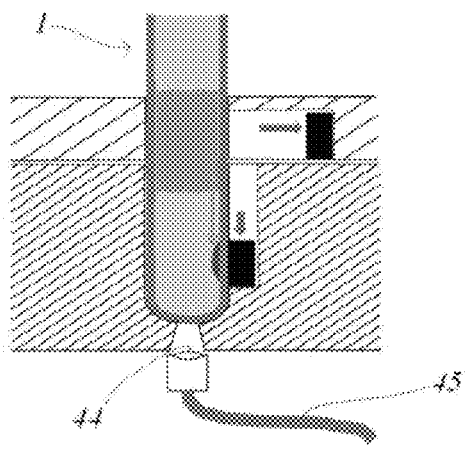
FIG. 7C is a longitudinal-sectional view of a part including the operation pipe held on the holding part.

The holding substrate may have an optical detection port. The optical detection port is arranged to be capable of irradiating an excitation light into the recovery portion B, and detect a signal derived from the target components or components related thereto which is emitted in the treatment or reaction in the recovery portion B. For example, as shown in FIGS. 7A to 7C, the optical detection port 71 can be formed to penetrate the holding substrate from the lower end of the holding hole 52 and has an aperture smaller than the outer diameter of the pipe portion b held by the holding hole 52. An optical detection part (including a fluorescence detection lens 44 and an optical fiber cable 45 in FIGS. 7A to 7C) may be arranged in the optical detection port 71. The position of the optical detection port is not limited to the position in FIGS. 7A to 7C, and for example, photometry from the side surface of the recovery portion may be considered.

[8. Magnetic Field Applying Part]

The magnetic field applying part and the magnetic field moving mechanism thereof that cause variations of the magnetic field for moving the magnetic particles in the operation pipe together with the target components are not particularly limited. As the magnetic field applying part, a magnetic source such as a permanent magnet (for example, a ferrite magnet or a neodymium magnet) or an electromagnet can be used. Outside the operation pipe, the magnetic field applying part can be disposed close to the operation pipe to such a degree that it is possible to aggregate the magnetic particles dispersed in the aqueous liquid layer in the operation pipe on the transport surface side of the pipe and transport the magnetic particles that are aggregated in the gel layer in the operation pipe. Accordingly, the magnetic field applying part can effectively generate a magnetic field for the magnetic particles via the transport surface of the pipe, and capture and transport the target components together with the magnetic particle mass.

[8-1. Shape]

The shape of the magnetic field applying part is not particularly limited. For example, it may be a massive magnetic field applying part that can generate a magnetic field at one point or a part of the operation pipe (for example, illustrated as the magnet 31 in FIGS. 3A to 3O or FIGS. 4A to 4H). More specifically, the magnetic field applying part may be cylindrical (for example, a diameter of 1 mm-5 mm, a thickness of 5 mm-30 mm). In the case of this shape, the magnetic field applying part can generating a magnetic field inside the operation pipe by being attached to one point or a part of the outer periphery of the operation pipe. On the other hand, the magnetic field applying part may be a ring-shaped magnet having a substantially-circular-centre hole and capable of generating a magnetic field around the operation pipe having a substantially circular cross section. In the case of this shape, the magnetic field applying part can generate a magnetic field inside the operation pipe by making the operation pipe pass through the substantially-circular-centre hole of the ring. In this case, since the magnetic field applying part having a ring shape surrounds the operation pipe, the magnetic particles also have a ring shape according to the shape of the magnetic field applying part when the magnetic particles are aggregated. On the other hand, if the shape of the magnetic field applying part is a massive shape, the aggregation shape of the magnetic particles is also a massive shape. In other words, when the magnetic field applying part having a ring shape is used, it is preferable in terms that a contact area between the magnetic particles and the aqueous liquid is larger and thus the target components and the like adsorbed on the magnetic particles can be more efficiently exposed in the liquid constituting the aqueous liquid layer.

[8-2. Magnetic Field Moving Mechanism]

[8-2-1. Movement in Longitudinal Direction of Control Pipe]

The magnetic field moving mechanism of the magnetic field applying part can move, for example, the magnetic field in the longitudinal direction (axial direction, at least downward direction) of the operation pipe in a state that the aggregation form of the magnetic particles can be maintained. When described as a magnetic field moving mechanism below, the mechanism can determine the stop position and control the moving speed, and the control may be performed manually or may be performed automatically by a computer and the like. The moving speed may be, for example, 0.5 mm-10 mm per second. The magnetic field moving mechanism is preferably a mechanism that can physically move the magnetic field applying part itself in the longitudinal direction of the operation pipe. The magnetic field moving mechanism can move the magnetic field applying part (permanent magnet 31 in FIGS. 3A to 3O and FIGS. 4A to 4H) itself as shown in FIGS. 3A to 3O and FIGS. 4A to 4H in the vertical direction. In addition, even in a device capable of concentrating a plurality of operation pipes as shown in FIG. 5, the magnetic field applying part (movable magnet plate 53 in FIG. 5) can be moved in the vertical direction (the magnetic field moving mechanism itself is not shown in any of the above cases).

[8-2-2. Control of Magnetic Field Intensity]

The magnetic field moving mechanism of the magnetic field applying part may be a mechanism that can variably control the intensity of the magnetic field applied to the magnetic particles. Specifically, the magnetic field can be blocked or attenuated. The degree of blocking or attenuation of the magnetic field is preferably a degree at which the aggregated magnetic particles can be dispersed in the droplet (the above item 6-2). For example, in the case of an electromagnet, an energization control part can be used to block the magnetic field. In addition, for example, in the case of a permanent magnet, a mechanism that can move a magnet disposed outside the operation pipe away from the operation pipe can be used. This mechanism may be controlled manually or automatically. The magnetic particles can be naturally dispersed in the aqueous liquid layer by attenuating the magnetic field applied to the magnetic particles, preferably by releasing the magnetic particles from the magnetic field. Accordingly, the target components or the accompanying components adsorbed on the magnetic particles can be sufficiently exposed in the liquid constituting the aqueous liquid layer.

[8-2-3. A Case of Device in which a Plurality of Control Pipes is Concentrated]

Figure 6:
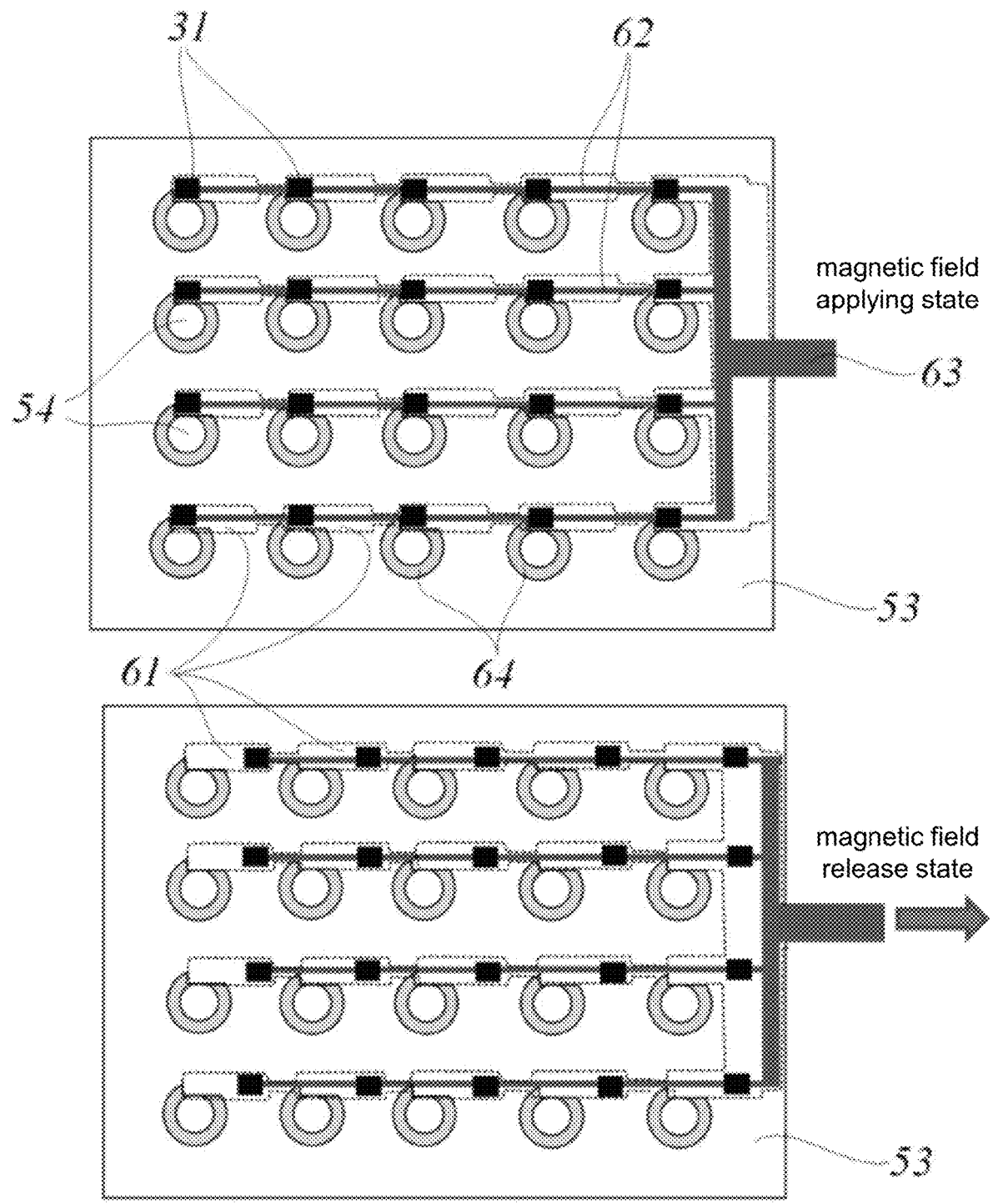
FIG. 6 is a cross-sectional view of a variation example of a magnetic field applying part (movable magnet plate) shown in FIG. 5.

As illustrated in FIG. 5, in a device in which a plurality of operation pipes 1 is concentrated, a plurality of magnetic sources corresponding to the plurality of operation pipes can be held by being unitized into one member that can move in the longitudinal direction of the operation pipe. As illustrated in FIG. 5, this unitized member can be embodied as the movable magnet plate 53 which is a magnetic field applying part that can move in the longitudinal direction of the operation pipe 1. As illustrated in FIG. 6, the movable magnet plate 53 in FIG. 5 includes a movable substrate that can move in the longitudinal direction of the operation pipe and a magnetic source (magnet 31) held in the movable substrate, and can be held in a state that a plurality of magnets 31 corresponding to each of the operation pipes is disposed. In addition, the member may or may not have a function of holding the operation pipe as the holding part described above. In the case illustrated in FIG. 5, a holding hole 54 corresponding to the operation pipe 1 is formed and thereby the movable magnet plate 53 can also have a holding function. In the illustration of FIG. 6, the magnetic field applying part is shown as a massive part, but the magnetic field applying part may have a ring shape being hollow corresponding to the holding hole 54.

As illustrated in FIG. 5, in the device in which the plurality of operation pipes 1 is concentrated, the magnetic field moving mechanism of the magnetic field applying part may be capable of simultaneously controlling the intensity of the magnetic field obtained by the magnetic field applying part in each of the plurality of operation pipes. For example, when a plurality of different magnetic field applying parts is used for each of the plurality of operation pipes, the magnetic field moving mechanism may be capable of simultaneously controlling the magnetic fields generated by the plurality of magnetic field applying parts.

In this member, when an electromagnet is used as the magnetic field applying part, the magnetic field can be controlled by current control. On the other hand, when a permanent magnet is used as the magnetic field applying part, in the above member, for example, it is possible to provide a mechanism that brings the member itself closer to or away from the operation pipe (for example, the member itself is moved substantially perpendicular to the longitudinal direction of the operation pipe), or inserts a magnetic shield material therebetween, or brings the plurality of magnetic field applying parts held in the member closer to or away from the operation pipe at a time without moving the member itself.

As illustrated in FIG. 6, the movable magnet plate 53 in FIG. 5 can be filled in a magnet holding portion 61 in a state that the magnet 31 corresponding to each operation pipe held in the holding hole 54 is disposed. The magnet holding portion 61 is formed in a size that allows the movement of the magnet 31 in the movable magnet plate 53 (that is, a movement of bringing the magnet 31 closer to or away from the operation pipe). As illustrated in FIG. 6, a plurality of magnets 31 can be connected to each other by connection rods 62, and all the connection rods 62 can be coupled to a handle member 63. By moving the handle member 63, as shown in FIG. 6, it is possible to bring all the magnets closer to the operation pipe (magnetic field applying state) and away from the operation pipe (magnetic field release state).

When the magnet is ring-shaped and this magnet is used to control the intensity of the magnetic field, for example, the magnet that is configured by two or more arc-shaped magnet parts and thereby formed into a ring shape can be used as the ring-shaped magnet. This ring-shaped magnet can release the operation pipe from the magnetic field by being divided substantially perpendicular to the diameter direction.

[8-2-4. Movement of Magnetic Field Applying Part in Holding Part Capable of Holding Recovery Portion B]

The holding part may have a recess in which the magnetic field applying part can move in the longitudinal direction of the pipe portion b. More specifically, the holding part may have, in a portion holding the recovery portion B, a recess in which the magnetic field applying part can move in the longitudinal direction of the pipe portion b. The magnetic field applying part that moves in the recess may be the same as or different from the magnetic field applying part contributing to the operation in the operation portion A. For example, as shown in FIG. 7A, a recess 72 is formed in the holding substrate 51 (in FIGS. 7A to 7C, the holding substrate 51 is configured by a temperature control block) equipped with the holding hole 52, and the recess is filled with a magnet 31' in advance. The movable magnet plate 53 on which the magnet 31 is disposed descends, and as shown in FIG. 7B, the movable magnet plate 53 is in contact with the holding substrate 51 and cannot move further downward. That is, depending on the magnet 31, the magnetic particles 6 cannot be transported further downward. At this time, the magnet 31' filled in the recess 72 of the holding substrate 51 is attracted to the magnet 31 by the magnetic field exerted by the magnet 31 on the movable magnet plate 53. Then, the magnetic particles 6 in the operation pipe 1 are attracted to both the magnet 31 and the magnet 31'. Next, as shown in FIG. 7C, when the magnet 31 in the movable magnet plate 53 is moved away from the operation pipe 1, the magnet 31' is released from the magnetic field generated by the magnet 31 and thus falls into the recess 72 due to gravity. At this time, the magnetic particles in the operation pipe 1 can be transported into the aqueous liquid $4l_2$ in the recovery portion B and be lowered near the bottom in the recovery portion B due to effects of the magnetic field of the magnet 31'. Accordingly, the magnetic particles can be delivered by the magnet 31 and the magnet 31', and the magnetic particles accompanied by the target components can be sufficiently exposed in the lowermost layer in the operation pipe.

[8-2-5. Magnetic Field Fluctuations]

The magnetic field moving mechanism may include a mechanism that enables a fluctuation motion such as an amplitude movement and rotation of the magnetic field. For example, it is possible to substitute a stirrer by providing a function that enables the magnetic force source to perform an amplitude motion (vertical motion) in the longitudinal direction of the operation pipe. Thereby, mixing or stirring in the aqueous liquid is facilitated. For example, in a case without the function of blocking or attenuating the magnetic field, the magnetic field applying part is made to reciprocate in the vertical direction for several times within the width of the thickness of the aqueous liquid layer while being kept close to the operation pipe (while the magnetic particles are aggregated), and thereby the target components and the like adsorbed on the magnetic particles in the aqueous liquid can also be sufficiently exposed in the liquid constituting the aqueous liquid layer.

[8-2-6. Temperature Control Function]

The magnetic field applying part may further have a temperature control function. For example, in FIGS. 4A to 4H, the temperature control function is schematically shown as 42.

Alternatively, a heater can be incorporated in the magnetic field applying part. By the latter temperature control function, the reagent temperature in the aqueous liquid layer at the position where the magnetic particles are present can be arbitrarily adjusted. For example, a case is described in which the operation pipe shown in FIGS. 4A to 4H is held by the holding part (holding substrate) as shown in FIGS. 7A to 7C and having the temperature control function as described in the above 7-3. In the operation pipe shown in FIGS. 4A to 4H, the recovery portion B fills multilayers including the RT reaction liquid layer $4l_1$ and the PCR reaction liquid layer $4l_2$ via the gel layer $4g$ as a recovery medium. When the operation pipe of FIGS. 4A to 4H is held by the holding substrate 51 as shown in FIGS. 7A to 7C, the portion directly held in the holding hole 52 of the holding substrate 51 may be only approximately a portion corresponding to the lowest layer of the operation pipe (PCR reaction liquid layer $4l_2$). In this case, since the portion filled with the RT reaction liquid layer $4l_1$ in which the reverse transcription reaction is performed is separated from the PCR reaction liquid layer $4l_2$ held directly on the holding substrate 51, it is difficult to add temperature control using the holding substrate 51.

Therefore, the device of the disclosure can have a temperature control function different from the temperature control function in the holding part. For example, as illustrated as 42 in FIGS. 4A to 4H, the temperature control function may not be interlocked with the magnetic field applying part; alternatively, as illustrated as 64 in FIG. 6, the temperature control function may be incorporated in the movable magnet plate 53 which is a magnetic field applying part and thereby be interlocked with the magnetic field applying part. In a specific aspect of the movable magnet plate 53 shown in FIG. 6 in which the temperature control function (heater) is incorporated, a heater 64 has an annular shape enclosing the holding hole 54. When the movable magnet plate 53 has the temperature control function in this way, in a period in which the movable magnet plate 53 is in a position filled with the RT reaction liquid layer $4l_1$ (FIG. 7A), the RT reaction liquid layer $4l_1$ is heated by the heater 64 in the movable magnet plate 53 and the optimum temperature (for example, 50° C.) can be achieved.

[9. Optical Detection Part]

The optical detection part is not particularly limited and can be easily selected by those skilled in the art corresponding to the analysis method in which the target components are supplied. For example, a part can be used which appropriately includes a light generation portion, a detection part, a light transmission part, a personal computer and the like. For example, in a case of the fluorescence detection part 41 shown in FIG. 4H, as shown more specifically in FIGS. 7A to 7C, incidence from the light generation portion (not shown) to the detection part (the light transmission part attached to a detection lens 44 (the optical fiber cable 45)) is performed, and light irradiation to the reaction liquid 4 in the operation pipe 1 through the detection lens 44 can be performed. The optical signal detected by the detection lens 44 can be sent to a light receiving element by the optical fiber cable 45, converted into an electrical signal, and then transmitted in real time to a personal computer (not shown), and changes in the fluorescence intensity of the reaction liquid 4 can be monitored. This is suitable when the disclosure performs a reaction or treatment such as a real-time nucleic acid amplification reaction in which a variable fluorescence intensity is detected.

An LED, a laser, a lamp or the like can be used as the light generation portion. In addition, in the detection, various light receiving elements from inexpensive photodiodes to photomultiplier tubes aiming at higher sensitivity can be utilized without particular limitation. For example, when a case in which a nucleic acid-related reaction such as a real-time nucleic acid amplification reaction or a nucleic acid-related treatment is performed is used as an example, when SYBR (registered trademark) GREEN I is used, this dye is specifically bound to a double-stranded DNA and generates fluorescence around 525 nm, and thus the detection part can detect a light having a target wavelength by cutting lights having wavelengths other than the target wavelength with an optical filter. In addition, when a case in which the nucleic acid amplification reaction using droplet movement is performed in the operation pipe is used as an example, the fluorescence observation of the droplet supplied to the nucleic acid amplification reaction can be performed in a darkroom in a state that excitation lights are irradiated to a temperature position in which an extension reaction (usually about 68-74° C.) using DNA polymerase is performed and the liquid droplet is stopped in this position. Furthermore, when an irradiation range of the excitation light is expanded from a temperature position in which heat denaturation is performed to a temperature position in which annealing is performed, the droplet can be moved and a melting curve of the amplification products can also be obtained.

EXAMPLE

Next, examples are given to describe the disclosure in more detail, but the scope of the disclosure is not limited hereto.

Example 1

[Nucleic Acid Extraction and Purification from Blood]

A gelling agent (Taiyo Chemical Co., Ltd., TAISET 26) is added to silicon oil (Shin-Etsu Silicone KF-56) to reach a ratio of 1.2% (weight ratio) and heated to 70° C. to be completely mixed with the silicon oil. A required amount of the oil mixed into a sol state and a required amount of necessary reagents are alternately injected and multi-layered from the tip of the injection needle into the operation pipe (consisting of a capillary (operation portion A) and a sample tube (recovery portion B)) shown in FIG. 3A in a manner that bubbles do not enter. When the capillary having an inner diameter of 1.5 mm is used, respectively 10 μL of the gel plug, 15 μL of the cleaning liquid (200 mM of KCl), and 20 μL of the elution liquid (10 mM of TrisHCl, 1 mM of EDTA pH 8.0)) are filled as shown in FIG. 3A. The filled capillary is placed at room temperature for 30 minutes to completely gel the gel plug. The upper end of the capillary forms a funnel-shaped sample supply port that is sealed by a film material and is sealed by a septum.

The uppermost layer in the capillary is made into 100 μL of a cell lysate (4M guanidine thiocyanate, 2% (w/v) of Triton X-100, and 100 mM of Tris-HCl pH 6.3) and contains 500 μg of silica-coated magnetic particles (nucleic acid extraction kit, MagExtractor-Plasmid-attached magnetic particles of Toyobo). Besides, as a nucleic acid isolation method using silica particles and chaotropic salts, a method disclosed by Boom et al. (Japanese Patent Laid-Open No. 2-289596) is used.

FIGS. 3B-3O are diagrams showing a nucleic acid extraction process from blood for each operation of the magnet. Finally, the nucleic acid is recovered in the elution liquid in the sample tube attached to the lower end of the capillary. In FIG. 3B, 200 μL of whole human blood is injected by an injection needle and is gently mixed with the magnetic particles by pipetting. After five minutes, as shown in FIGS. 3C and 3D, the magnetic particles are collected by bringing the magnet close from one side of the capillary, and the magnet is lowered at a speed of 0.5 mm per second. After the magnetic particles pass through the gel plug, as shown in FIG. 3E, the magnet is separated from the capillary. As shown in FIGS. 3F-3M, the same cleaning is performed for three times. Thereafter, the magnet is released as shown in FIG. 3N, and the magnetic particles are dropped into the tube containing the elution liquid. After one minute, the magnet is brought close again to collect the magnetic particles, and as shown in FIG. 3O, the magnet particles are retracted into the gel plug, and the nucleic acid extraction and purification operations are completed. In this example, 200 ng of DNA is obtained for 1 μL of the elution liquid.

Figure 8:
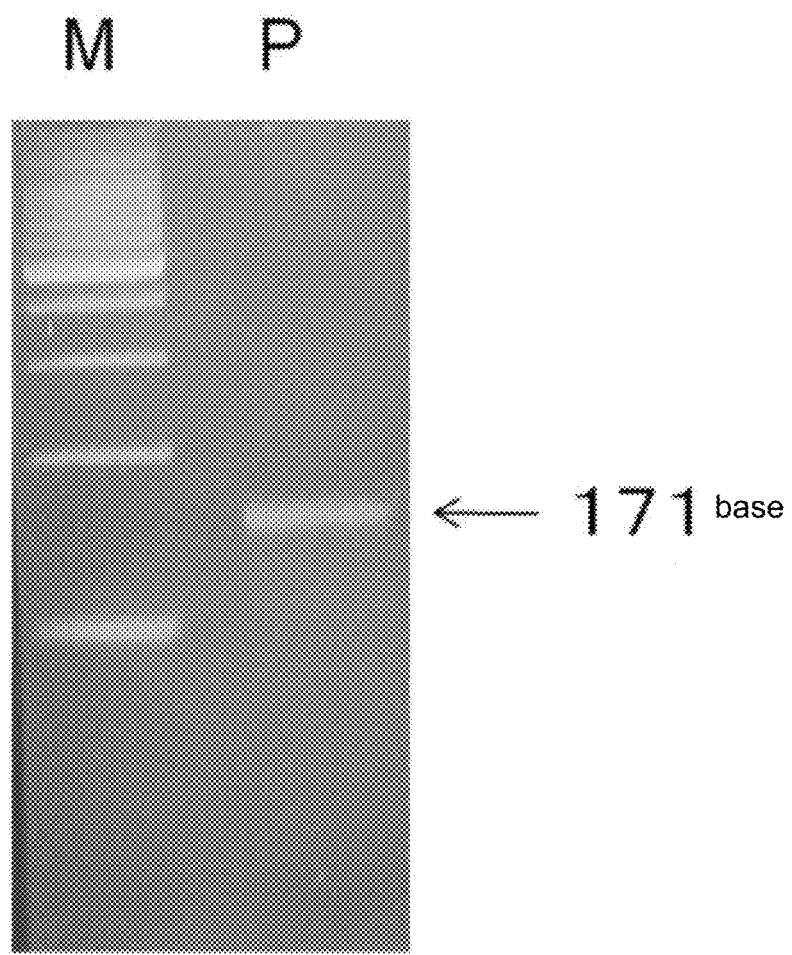
FIG. 8 is a result obtained in Example 1 in which the process shown in FIGS. 3A to 3O is performed.

The sample tube is removed from the capillary, 1 μL of the elution liquid obtained in the sample tube is used, and a PCR reaction mixture (10 μL of total reaction volume) containing 0.15 U of Taq DNA polymerase, 500 nM of human GAPDH gene detection primer(5'-GCGCTGC-CAAGGCTGTGGGCAAGG-3' (Sequence number 1) and 5'-GGCCCTCCGACGCCTGCTTCACCA-3' (Sequence number 2)) and 200 nM of dNTP is used to perform PCR (temperature cycle: 95° C., one second, 60° C., ten seconds, 72° C., ten seconds, 40 cycles) by a thermal cycler (ABI9700, Applied Biosystems). As a result, as shown in FIG. 8, a reaction product specific to the human GAPDH gene (fragment size 171 bases) is confirmed by agarose gel electrophoresis.

As described above, the disclosure is described according to the embodiments of the disclosure, but it should not be considered that the description and drawings constituting a part of this disclosure limit the disclosure. From this disclosure, various alternative embodiments, examples, and operational techniques are apparent to those skilled in the art. The technical scope of the disclosure is defined only by the invention specific matters of the scope of claims reasonable from the above description, and can be modified and embodied without departing from the scope in the implementation stage.

Sequence numbers 1 and 2 are synthetic primers.

What is claimed is:

1. A manufacturing method of an operation pipe for operating target components, comprising:
 providing a hollow pipe having a closable open end for supplying a sample containing the target components on one side and a closed end on the other side, and having an operation pipe portion on the open end side and a recovery pipe portion on the closed end side;
 filling a recovery medium in the recovery pipe portion so that a first gel layer and a first aqueous liquid layer which is in contact with the closed end are multi-layered, wherein the first aqueous liquid layer in contact with the closed end has a predetermined volume, a layer length of the first aqueous liquid layer in contact with the closed end varies with variations in an inner diameter of the hollow pipe or a length of the hollow pipe, and a volume of the first aqueous liquid layer in contact with the closed end is 50 µL-300 µL, and a layer length of the first gel layer is determined by a length in the longitudinal direction of the hollow pipe;
 filling an operation medium in the operation pipe portion so that second gel layers and second aqueous liquid layers are alternately multi-layered in the longitudinal direction of the hollow pipe, wherein a layer length of each of the second gel layers and a layer length of each of the second aqueous liquid layers are determined by the length in the longitudinal direction of the hollow pipe.

2. The manufacturing method of the operation pipe according to claim 1, wherein the inner diameter of the hollow pipe is 0.1 mm-5 mm.

3. The manufacturing method of the operation pipe according to claim 1, wherein the operation pipe portion and the recovery pipe portion are separable.

4. The manufacturing method of the operation pipe according to claim 1, wherein the material of the hollow pipe is selected from a group consisting of polyethylene, polypropylene, fluororesin, polyvinyl chloride, polystyrene, polycarbonate, acrylonitrile- butadiene-styrene copolymer, acrylonitrile-styrene copolymer, acrylic resin, polyvinyl acetate, polyethylene terephthalate, cyclic polyolefin, and glass.

5. The manufacturing method of the operation pipe according to claim 1, wherein an inner diameter of the open end is larger than an inner diameter of the operation pipe portion and an inner diameter of the recovery pipe portion.

6. The manufacturing method of the operation pipe according to claim 1, wherein the hollow pipe has optical transparency.

7. The manufacturing method of the operation pipe according to claim 1, wherein surface roughness of an inner surface of the hollow pipe is 0.1 µm or less.

8. The manufacturing method of the operation pipe according to claim 1, wherein the layer length of the first gel layer and the layer length of each of the second gel layers are 1-20 mm.

9. The manufacturing method of the operation pipe according to claim 1, wherein the layer length of each of the second aqueous liquid layers is 0.5-30 mm.

* * * * *